US009844355B2

(12) United States Patent
Keppel et al.

(10) Patent No.: US 9,844,355 B2
(45) Date of Patent: *Dec. 19, 2017

(54) OPPOSED VIEW AND DUAL HEAD DETECTOR APPARATUS FOR DIAGNOSIS AND BIOPSY WITH IMAGE PROCESSING METHODS

(71) Applicant: Hampton University, Hampton, VA (US)

(72) Inventors: Cynthia Keppel, Norfolk, VA (US); Douglas Kieper, Seattle, WA (US)

(73) Assignee: HAMPTON UNIVERSITY, Hampton, VA (US)

(*) Notice: Subject to any disclaimer, the term of this patent is extended or adjusted under 35 U.S.C. 154(b) by 714 days.

This patent is subject to a terminal disclaimer.

(21) Appl. No.: 14/338,837

(22) Filed: Jul. 23, 2014

(65) Prior Publication Data

US 2014/0334603 A1 Nov. 13, 2014

Related U.S. Application Data

(63) Continuation of application No. 13/647,916, filed on Oct. 9, 2012, now Pat. No. 8,855,748, which is a (Continued)

(51) Int. Cl.
*A61B 5/00* (2006.01)
*A61B 6/00* (2006.01)
(Continued)

(52) U.S. Cl.
CPC .............. *A61B 6/469* (2013.01); *A61B 6/037* (2013.01); *A61B 6/12* (2013.01); *A61B 6/502* (2013.01);
(Continued)

(58) Field of Classification Search
CPC ....... A61B 6/037; A61B 6/502; A61B 19/201; A61B 6/469; A61B 90/11; A61B 6/12;
(Continued)

(56) References Cited

U.S. PATENT DOCUMENTS 5,519,221 A 5/1996 Weinberg
6,377,838 B1 4/2002 Iwanczyk et al.
(Continued)

OTHER PUBLICATIONS

Hampton University, Office of Governmental Relations, Jul. 15, 2004, pp. 8-9.

(Continued)

*Primary Examiner* — Joel Lamprecht
(74) *Attorney, Agent, or Firm* — Leason Ellis LLP

(57) ABSTRACT

The invention relates generally to biopsy needle guidance which employs an x-ray/gamma image spatial co-registration methodology. A gamma camera is configured to mount on a biopsy needle gun platform to obtain a gamma image. More particular, the spatially co-registered x-ray and physiological images may be employed for needle guidance during biopsy. Moreover, functional images may be obtained from a gamma camera at various angles relative to a target site. Further, the invention also generally relates to a breast lesion localization method using opposed gamma camera images or dual opposed images. This dual head methodology may be used to compare the lesion signal in two opposed detector images and to calculate the Z coordinate (distance from one or both of the detectors) of the lesion.

18 Claims, 21 Drawing Sheets

Related U.S. Application Data continuation of application No. 13/467,655, filed on May 9, 2012, now Pat. No. 8,311,617, which is a continuation of application No. 12/688,509, filed on Jan. 15, 2010, now Pat. No. 8,200,316, which is a continuation of application No. 11/538,682, filed on Oct. 4, 2006, now Pat. No. 7,711,409.

(51) Int. Cl.
| A61B 6/03 | (2006.01) |
|---|---|
| A61B 6/12 | (2006.01) |
| A61B 90/11 | (2016.01) |
| A61B 90/00 | (2016.01) |

(52) U.S. Cl.
CPC .............. *A61B 90/11* (2016.02); *A61B 6/583* (2013.01); *A61B 2090/392* (2016.02); *A61B 2090/3908* (2016.02)

(58) Field of Classification Search
CPC ...... A61B 2090/3908; A61B 2090/392; A61B 6/583
See application file for complete search history.

(56) References Cited

U.S. PATENT DOCUMENTS

| 6,389,098 | B1 | 5/2002 | Keppel et al. | |
|---|---|---|---|---|
| 7,291,841 | B2 | 11/2007 | Nelson et al. | |
| 7,711,409 | B2* | 5/2010 | Keppel .................. | A61B 6/037 424/9.1 |
| 8,200,316 | B2* | 6/2012 | Keppel .................. | A61B 6/037 424/9.1 |
| 8,311,617 | B2* | 11/2012 | Keppel .................. | A61B 6/037 424/9.1 |
| 8,855,748 | B2* | 10/2014 | Keppel .................. | A61B 6/037 424/9.1 |

OTHER PUBLICATIONS

R. Pani et al., "Multi-PSPMT Scintillation Camera," IEEE Transactions of Nuclear Science, Jun. 1999, pp. 702-708, vol. 46, No. 3.
G.J. Gruber et al., "A Discrete Scintillation Camera Module Using Silicon Photodiode Readout of CsI(T1) Crystals for Breast Cancer Imaging," IEEE Trans. of Nuclear Science Jun. 1998, pp. 1063-1068, vol. 45, No. 3.
M. Williams et al., "Performance of a PSPMT Based Detector for Scintimammography", Phys. Med. Biol., 45 (2000), pp. 781-800.
S. Majewski et al., "Optimization of Dedicated Scintimammography Procedure Using Detector Prototypes and Compressible Phantoms", IEEE Transactions of Nuclear Science, Jun. 2001, pp. 822-829, vol. 48, No. 3.
R. Brem et al., "High-Resolution Scintimammography: A Pilot Study", The Journal of Nuclear Medicine, Jul. 2002, pp. 909-915, vol. 43, No. 7.
A.G. Weisenberger et al., "Small Field of View Scintimammography Gamma Camera Integrated to a Stereotatic Core Biopsy Digital X-Ray System", IEEE Transactions of Nuclear Science; Oct. 2002, pp. 2256-2261, vol. 49, No. 5.
R. Raylman et al., "Positron Emission Mammography—Guided Breast Biopsy," The Journal of Nuclear Medicine, Jun. 2001, pp. 960-966, Vo. 42, No. 6.
R. Raylman et al., "The Potential Role of Positron Emission Mammography for Detection of Breast Cancer. A Phantom Study," Med. Phy., Aug. 2000, pp. 1943-1954, vol. 27 No. 8.

M.F. Smith et al., "Aspects of 3-D Imaging by Classical Tomography for Dual Detector PEM," Thomas Jefferson Nat'l Accelerator Facility and Dept. of Radiology, Va. Commonwealth Univ. Health System, Livermore Berkeley Lab, lbl.gov/3D2001/abstracts/111. pdf, unknown publicatin dated (if pblished), 4 pages.
R. Raylman et al., "Corrections for the Effects of Accidental Coincidences, Compton Scatter, and Object Size in Positron Emission Mammography (PEM) Imaging," IEEE Transactions of Nuclear Science, Jun. 2001, pp. 913-923, vol. 48 No. 3.
M.F. Smith et al., "Analysis of Factors Affecting Positron Emission Mammography (PEM) Image Formation," IEEE Tran. of Nuclear Sci., Feb. 2003, pp. 53-59, vol. 50 No. 1.
Dilon Technologies, "The Dilon 6800 Gamma Camera: Smaller Detector Optimizes Results of Breast Imaging," 2007, 3 pages.
Lifespan, "Breast Imaging Stereotactic Breast Biopsy," 2007, 3 pages.
Faslodex, "Stereotactic Biopsy: Did the Radiologist Get it Right?," John Hopkins University, May 25, 2007, 2 pages.
Strong Health, "Women's Health," Stereotactic Breast Biopsy, Dec. 11, 2007, 3 pages.
Suros Surgical Systems, Inc., A Hologic Company, "Compassionate Technology," Automated Tissue Excision and Collection (ATEC) System and Suros Celero Device, B-SUROS-001 Jan. 2007, 10 pages.
Hologic, "Digital Mammography Bone Densitometry Breast Biopsy Mini C Arm," 2005, Suros Surgical Systems, 3 pages.
Siemens, "Siemens Medical Solutions," Siemens, AG, 2007, 7 pages.
Ethicon, "Innovative Solutions for Better Health," Ethicon, Inc., Nov. 8, 2007, 1 page.
Gamma Medica, "Gamma Medica-Ideas," 2007, 8 pages.
Naviscan PET Systems, "PEM Flex Solo II," 2007, 7 pages.
E. Levine et al., Positron Emission Mammography: Initial Clinical Results, Annals of Surgical Oncology, 2003, pp. 86-91, vol. 10, No. 1.
C. Thompson et al., "Positron Emission Mammography (PEM): A Promising Technique for Detecting Breast Cancer," IEEE Transactions of Nuclear Science, Aug. 1995, pp. 1012-1017, vol. 42, No. 1
C.J. Thompson et al., "Feasibility Study for Positron Emission Mammography," Medical Physics, Apr. 1994, pp. 529-538, vol. 21, No. 4.
R. Rayiman et al., "PEM Stereotactic Breast Biopsy," West Virginia University and Jefferson Lab, Jun. 30, 2005, 2 pages.
A. Karimian et al., "CYBPET: A Cylindrical PET System for Breast Imaging," Nuclear Instruments and Methods in Physics Research A 545, 2005, pp. 427-435.
J.L. Robar et al.,"Construction and Calibration of Detectors for High-Resolution Metabolic Breast Cancer Imaging,"Mucl. Instr. And Meth. In Phys. Res., 1997,pp. 402-406, A 392.
K. Murthy et al., "Results of Preliminary Clinical Trials of the Positron Emission Mammography System PEM-I: A Dedicated Breast Imaging System Producing Glucose Metabolis Images Using FDG," The Journal of Nuclear Medicine, Nov. 2000, pp. 1851-1858, vol. 41, No. 11.
Gamma Medica Press Release, "Lumagem Identifies Breast Cancer Missed by all other Modalities," Nov. 23, 2001, 1 page.
G. Schwartz, "Solid Circumscribed Carcinoma of the Breast," Annals of Surgery, vol. 169, No. 2, Feb. 1969, pp. 165-173.
G. Schwartz et al., "Lumpectomy and Level I Axillary Dissection Prior to Irradiation for "Operable" Breast Cancer," Annals of Surgery, Oct. 1984, pp. 554-559, vol. 200 No. 4.
G. Schwartz et al., "Clinically Occult Breast Cancer," Annals of Surgery, Jan. 1980, pp. 8-12, vol. 191, No. 1.
Anne L. Rosenberg et al., "Clinically Occult Breast Lesions: Localization and Significance," Radiology, Jan. 1987, pp. 167-170, vol. 162 No. 1.

* cited by examiner

OPPOSED VIEW AND DUAL HEAD DETECTOR APPARATUS FOR DIAGNOSIS AND BIOPSY WITH IMAGE PROCESSING METHODS

CROSS-REFERENCE TO RELATED APPLICATIONS

This is a continuation of co-pending U.S. Non-Provisional patent application Ser. No. 13/647,916 filed on Oct. 9, 2012 which is a continuation of U.S. Non-Provisional patent application Ser. No. 13/467,655, filed May 9, 2012, now U.S. Pat. No. 8,311,617 which is a continuation of U.S. Non-Provisional patent application Ser. No. 12/688,509, filed Jan. 15, 2010, now granted as U.S. Pat. No. 8,200,316 issued Jun. 12, 2012 which is a continuation of U.S. patent application Ser. No. 11/538,682 filed Oct. 4, 2006, now granted as U.S. Pat. No. 7,711,409 on May 4, 2010, entitled OPPOSED VIEW AND DUAL HEAD DETECTOR APPARATUS FOR DIAGNOSIS AND BIOPSY WITH IMAGE PROCESSING METHODS, the disclosures of which are incorporated by reference herein in their entirety.

BACKGROUND

Field of the Invention

The invention relates generally to biopsy needle guidance by employing an x-ray/gamma image spatial co-registration methodology. Further, the invention relates to using a plurality of gamma camera images taken at different positions to identify breast lesion location. Moreover, the invention also generally relates to a breast lesion localization method using opposed gamma camera images or dual opposed images.

Related Art

X-ray imaging of the breast provides high spatial resolution images of changes in breast tissue density. These density changes may be due to a number of factors such as age, pre- and post-menopausal tissue changes and the presence of various pathological conditions. X-ray imaging is a commonly used technique for breast cancer screening and diagnosis, but since it also is sensitive to other non-malignant pathologies, its accuracy is compromised. The specificity of x-ray imaging may be quite poor with only about 20% to about 35% of biopsies yielding cancer diagnoses. It is also a commonly used modality for breast tumor needle biopsy guidance, but has been found to be lacking in target accuracy for some cases.

Nuclear medicine breast imaging techniques may yield accurate physiological data, but with a lower spatial resolution than that obtained with x-ray imaging. This physiological imaging is much more specific than x-ray imaging, with about 70% of positive studies yielding a cancer diagnosis. Also, since it detects physiological abnormalities, it directly indicates the location of disease, while x-ray imaging is limited to detecting changes in tissue density which may be secondary to the presence of disease.

Another important area of diagnostic concern is the accuracy of a stereotactic needle biopsy. This biopsy procedure has been proven to be effective in managing most patients demonstrating suspicious mammographic findings in screening mammograms. Due to its less invasive nature, this procedure may be more desirable to perform than other biopsy procedures. Despite the promising role of this procedure in breast lesion management, however, some clinical studies have found a false negative rate of about 10%. Moreover, findings from additional studies point toward specific subgroups limiting the diagnostic accuracy of this procedure. The first of these subgroups consists of cases in which the needle biopsy underestimated the extent or type of disease. In these studies, needle biopsies indicating atypical ductal hyperplasia or ductal carcinoma in-situ were often upgraded to infiltrating ductal carcinoma upon open biopsy or follow-up. In addition, another study found that the diagnostic accuracy of needle biopsy was dependent on lesion size, as masses larger than about 3 cm were less likely to be diagnosed correctly.

Scintimammography is a functional, biomolecular breast imaging procedure that is typically conducted with large field-of-view gamma cameras. The efficacy of this procedure is lacking for diagnostic accuracy for lesions less than about 1 cm in diameter, non-palpable masses, and lesions located in the medial aspect of the breast. Several investigators have hypothesized that these limitations may be due to the use of non-optimized large field-of-view detectors and suggested the study accuracy could be improved with dedicated small field-of-view systems. Such systems may allow the breast to be compressed against the collimator to optimize image spatial resolution. In addition, these detectors may be positioned to allow the breast to be imaged from several angles including the medial views. Improved spatial resolution may lead to improved lesion visibility and therefore higher sensitivity. Accordingly, there is a need to improve the exiting imaging methodologies and techniques.

SUMMARY OF THE INVENTION

The invention satisfies the above needs and avoids the disadvantages and drawbacks of the prior art by spatially co-registering and fusing gamma images and x-ray images together to create a single image. This takes advantage of both the high spatial resolution of the x-ray image and the high specificity of the nuclear medicine data. This fused image also allows tumor localization with either or both modalities.

According to a principle of the invention, a gamma camera may be removably attached to a biopsy needle gun platform, thereby permitting control of the acquisition of one or more functional images. The biopsy needle gun may be reattached and one or more biopsies are performed based on a co-registered imaged resulting from fusing an x-ray image and a functional image.

According to another principle of the invention, multiple functional images using a gamma camera at multiple positions may be obtained. The functional images are then registered together to create a spatially co-registered image for tumor and lesion localization and biopsy needle gives guidance and control.

According to a further principle of the invention, functional images at opposing angles may be obtained. The functional images are then evaluated to determine a three-dimensional location of a tumor.

The invention may be implemented in a number of ways. According to one aspect of the invention, a method for lesion localization in a target site of a patient is provided. According to this aspect a first image from an imaging device located at a first image position is obtained; a second image from an imaging device located at a second image position is then obtained and an X coordinate of the lesion within the target site of the patient based upon the first image and the second image is calculated, a Y coordinate of the lesion within the target site of the patient based upon the first image and the second image is calculated, and a Z coordinate of the lesion within the target site of the patient based upon the first image and the second image is calculated. In a further aspect, radiotracer uptake may be calculated based upon the X, Y, and Z coordinates. Calculating the Z coordinate of the lesion may include comparing the comparative signal intensity and the spatial resolution data in the first image and the second image.

In an additional aspect, the first image may be generated by a first x-ray detector and the second image may be generated by a second x-ray detector positioned about 180° relative to the first x-ray detector. Alternatively, the second image may be generated by a gamma camera positioned about 180° relative to the first x-ray detector. Furthermore, the second image may be generated by a gamma camera positioned about 180° relative to the first gamma camera.

In another aspect of the invention, the target site may be the breast, thyroid, parathyroid, heart, liver, kidney, gall bladder, bladder, reproductive organs and glandular structures.

Another aspect of the invention provides an apparatus for determining lesion location within a target site in a patient. The apparatus may include at least one gantry; and at least one imaging device mounted on the at least one gantry, where the at least one imaging device may be movable with respect to the target area of the patient such that the at least one imaging device acquires a plurality of images at a plurality of positions relative to the target site in the patient. Furthermore, the apparatus may include a controller configured to control movement of the at least one imaging device, to be capable to receive images from the at least one imaging device, and to be capable to calculate the lesion location within the target site of the patient based upon the plurality of images generated from said at least one imaging device. Additionally, the apparatus may include a pair of compression paddles.

In a further aspect, the first imaging device may be an x-ray generator mounted on a first gantry and the second imaging device may be an x-ray detector mounted on the first gantry and the third imaging device may be a gamma camera mounted on a second gantry. In yet a further aspect, the apparatus may also include a fourth imaging device which is a gamma camera mounted on the second gantry.

An additional aspect provides that the first gantry and the second gantry may be concentric moveable rings with respect to each other. Furthermore, the first imagining device may be a gamma camera mounted on the first gantry, the second imaging device may be an x-ray generator mounted on the second gantry and the third imaging device may be an x-ray detector mounted on the second gantry. In an additional aspect, the fourth imaging device may be a gamma camera mounted on the first gantry. The first and second gantry may be concentric rings which are moveable with respect to each other.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced. In the drawings.

Figure 1:
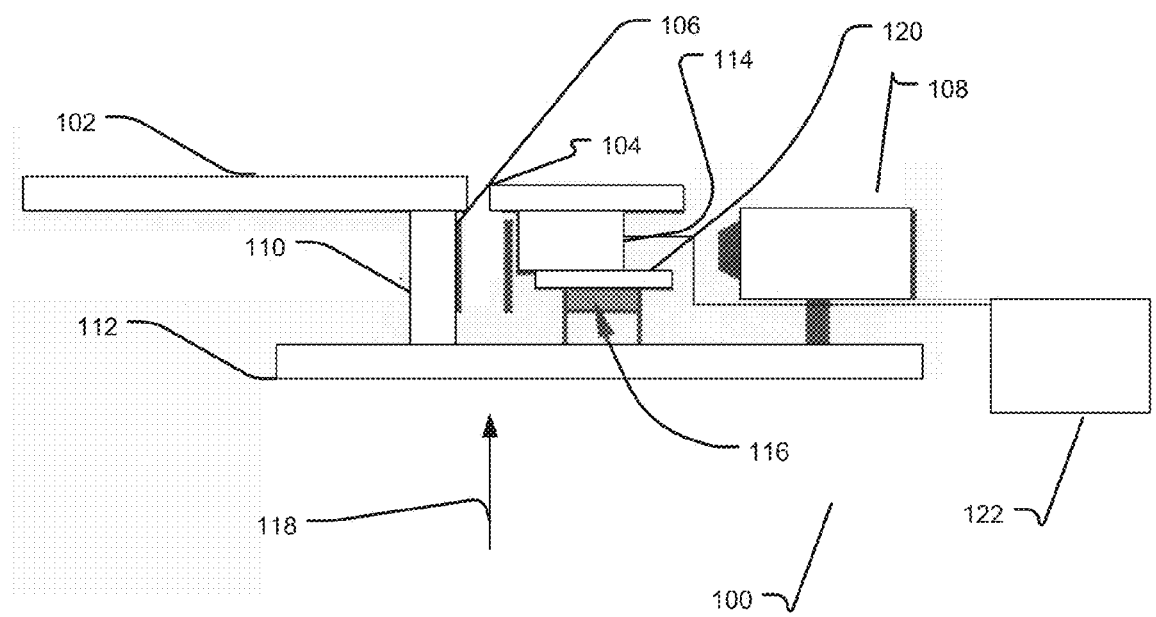
FIG. 1 is a schematic illustration of the detector system illustrating a gamma camera mounted to an existing x-ray stereotactic biopsy table constructed according to principles of the invention.

Linear fits for each data set were applied (true positive fits in solid lines and false positive fits in dotted lines). Note the positive slope of the true positive cases and the negative slope of the false positive cases.

DETAILED DESCRIPTION OF THE INVENTION

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is noted that as used herein and in the appended claims, the singular forms "a," "an," and "the" include the plural reference unless the context clearly dictates otherwise. Thus, for example, a reference to "a lesion" is a reference to one or more lesions and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

Definitions

PSPMT is position sensitive photomultiplier tubes.
FDG (F-18) or F-18 is fluoro-2-deoxyglucose.
PEM is positron emission mammography.
SPECT is single photon emission computed tomography.
ROI is region of interest.
BKG is baseline tissue uptake curve.
AOC is area of concern.
PPV is positive predictive value.
NPV is negative predictive value.
The term "radiopharmaceutical" generally refers to tracers used in the diagnosis and treatment of many diseases, including without limitation, breast cancer, and for imaging and function studies of the brain, myocardium, thyroid, lungs, liver, gallbladder, kidneys, skeleton, blood and tumors. Radiopharmaceuticals suitable for use with the invention may include but are not limited to, technetium (Tc-99m), FDG, sestaMlBl (Tc-94m), Tl-201 chloride, or any other imaging specific reagent.

The term "functional image" or "physiological data" generally refers to an image generated from detection of a radiopharmaceutical.

The term "non-functional image" or "anatomical data" generally refers to the image(s) generated by an x-ray detector.

"Patient" as used herein, refers to an individual who requires detection and diagnosis of possible disease, such as breast cancer. Furthermore, the term "subject" includes animals and humans.

"Target tissue," as used herein generally refers to any tissue in the body of any animal, including the human body that composes all the organs, structures and other contents. Specifically, a tissue is any substance made up of cells that perform a similar function with an organism. For example, tissue may refer to any epithelial tissue, breast tissue, connective tissue, muscle tissue, such as cardiac, smooth muscle, and skeletal, and any nervous tissue, such as tissue within the brain, spinal cord, and/or peripheral nervous system.

One aspect of the invention generally relates to a mounting mechanism to adapt a gamma camera (also referred to herein as a "detector head" or a "head") to a stereotactic needle core biopsy machine. Thus, a system is provided that employs the mechanical mount of the needle driver platform of a commercial stereotactic biopsy table to attach a small field-of-view gamma camera. This platform permits various needle guns to be utilized. Since the accuracy of biopsy is dependent on the mechanical alignment of this gun to the x-ray images, it is an excellent mounting surface for other devices requiring such alignment. By employing this mount as a stage for the gamma camera, the image taken by the gamma camera may be aligned with the image taken by the x-ray without the use of additional alignment tools. This method may allow image fusion and lesion localization by combining data generated from a gamma camera and digital x-ray detector. Further, this method uses spatially co-registered x-ray and physiological images for needle guidance during biopsy. Following imaging, the gamma camera may be removed from the mounting platform and replaced with the needle gun to implement the biopsy procedure. The biopsy may be performed based on the spatially co-registered image.

Additionally, the invention generally relates to a multiple angle stereotactic gamma guided biopsy system. This multiple angle system may be used to image the breast from multiple angles. Use of multiple heads may allow simultaneous imaging thereby reducing the stereotactic imagining time compared to a single head system. Also, the multiple angle system, when implemented using multiple heads, may allow dynamic radiotracer wash-in studies to be simultaneously viewed from multiple angles.

Moreover, another aspect of the invention generally relates to a breast lesion localization method using opposed gamma camera images or dual opposed images. This dual head methodology may be used to compare the lesion signal in two opposed detector head images and to calculate the Z coordinate (distance from one or both of the detectors) of the lesion. Other types of images may also be used. Moreover, the invention generally relates to a method for breast lesion uptake quantification using a dual head detector. This quantification method may be used to derive the radiotracer concentration within a specific volume of tissue from an opposed dual position gamma camera acquisition. Additionally, the dual head system may be used for image fusion and processing for increased lesion detectability, 3-dimensional localization, lesion radiotracer concentration and biopsy guidance.

According to an embodiment of the invention, a small field-of-view gamma camera is attached to the mechanical mount of the needle driver platform of a commercial stereotactic biopsy table, such as any conventional Lorad or Fischer-type stereotactic tables. The mechanical accuracy of this mount and its alignment with the x-ray detector allows the x-ray and gamma camera images to be co-registered reliably, and facilitates direct image fusion without the use of software alignment. Gamma cameras for use in the system of the invention have been described in U.S. Pat. No. 6,389,098, which is expressly incorporated herein by reference in its entirety. Since the detectors are mechanically aligned, this fusion process is straight forward and may allow the physician to evaluate both the anatomical data (x-ray) and the physiological data (gamma) in a single image to better determine the location of a lesion and therefore improve and/or optimize needle localization. It may also allow the localization to be calculated with the existing cursor system in the x-ray system if the gamma camera image is imported and fused to the x-ray image in the system software.

FIG. 1 is a schematic diagram of the detector system illustrating a gamma camera mounted to an existing x-ray stereotactic biopsy table according to principles of the invention. A system 100 for a core biopsy device is provided. In this embodiment, the system 100 includes a table 102, a hole or aperture 104, compression paddles 106, an x-ray generator 108, an x-ray detector 110, a support arm 112, a gamma camera 114, such as a scintimammography, gamma sensitive mini-camera, on a removable positioning stage 120, and a controller 122.

Referring back to FIG. 1, the table 102 may include an aperture or hole 104 for pendantly accepting the breast of a patient (not shown) lying face down on table 102. Below aperture 104 are conventional compression paddles 106 that receive and compress the breast under examination. Compression paddles can be solid or fenestrated for biopsy access. Also, the compression paddles can move in and out. An x-ray generator 108 and a x-ray detector 110, such a digital x-ray detector, are mounted at opposing ends of a platform 116 that is allowed to rotate about axis of rotation 118. A gamma camera 114 is located proximate compression paddles 106 and arranged to obtain one or more images that can be registered with those obtained by the x-ray generator 108 and the x-ray detector 110. The gamma camera may be removeably mounted on a positioning platform 120 that rotates about its axis of rotation 118 such that the gamma camera can be rotated out of any obstructing position during acquisition of the x-ray images and then rotated into position to obtain one or more images before or after acquisition of the x-ray images.

In using a system of the invention, the patient undergoing examination is first injected with a suitable radiopharmaceutical. Here, the system of the invention utilizes the higher uptake of certain radiopharmaceuticals by the organ or tissue of interest, thereby allowing the selected organ/tissue to be imaged. For example, malignant tissues preferentially absorb the radiopharmaceutical, such as Tc-99m, Sesta-MIBI, and Tl-201 chloride, in direct comparison to benign masses (except for some highly cellular adenomas). Therefore, these radiopharmaceuticals can be used to help diagnose and differentiate tumors from benign growths, for example in the system of the invention for breast cancer detection and diagnosis. Possible mechanisms for uptake of Tl-201 chloride into tumor cells include the action of the ATPase sodium-potassium transport system in the cell membrane which creates an intracellular concentration of potassium greater than the concentration in the extracellular space. Thallium may be significantly influenced by this transport system in tumors. In addition, a co-transport system has been identified which also is felt to be important in uptake of thallium by tumor cells.

Following injection of the radiopharmaceutical, the patient is placed on the above-described examination table 102 with one breast extending through aperture 104. The paddles 106 are compressed about the breast in the conventional fashion, and one or more X-ray images are acquired in the conventional manner while gamma camera 114 is moved out of the field of view of X-ray detector 110. Gamma camera 114 is then moved into position and one or more images are acquired with gamma camera 114.

A further embodiment of the invention generally relates to a method for image fusion and lesion localization by combining data from a gamma camera and an x-ray detector. A computer software program to spatially co-register the images obtained by each of these modalities and fuse the data to form a single image containing physiological and anatomical information is employed. Representative computer software programs may include IDL (RSI, Boulder, Co), Nuc-med image, and O-sirus. Once the X-ray image(s) are registered electronically with the gamma image(s), any lesions and their location may be positively located.

Figure 2:
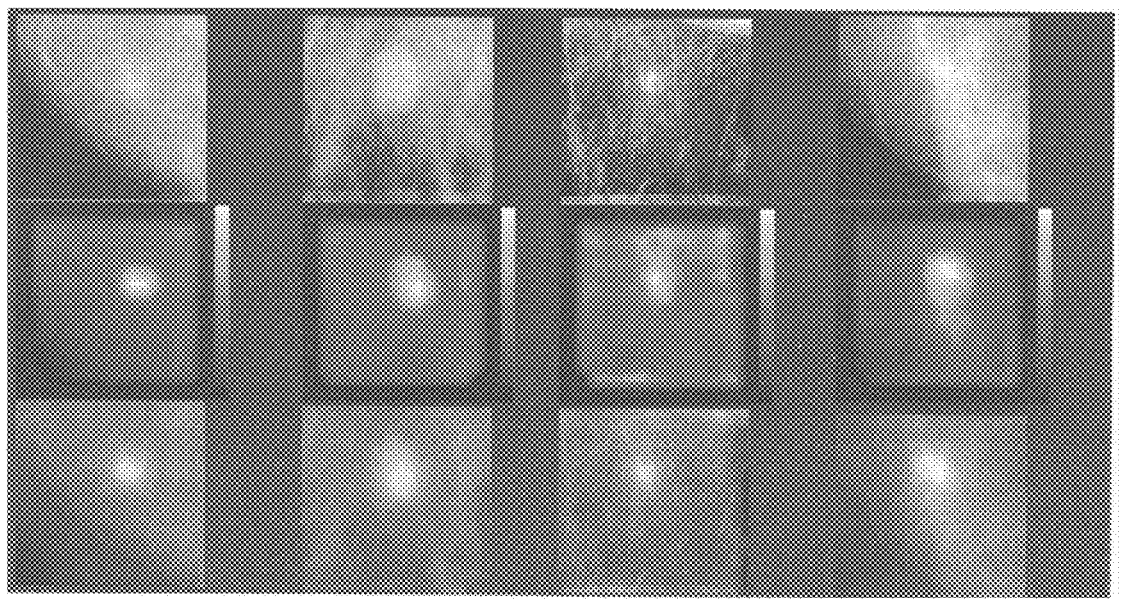
FIG. 2 illustrates resulting x-ray images, gamma camera images and co-registered images from a patient study implemented according to principles of the invention.

FIG. 2 illustrates resulting x-ray images, gamma camera images and co-registered images from a patient study described in specific example 3, infra, implemented according to principles of the invention. According to an embodiment of the invention, both the x-ray images and the gamma images are digital, as is the resulting co-registered image. Because of the higher malignancy determination capability of the gamma camera, better decisions can be made as to whether a biopsy by any conventional method is required and what biopsy method should be used. A method according to principles of the invention may use the spatially co-registered x-ray and gamma (nuclear medicine) images for needle guidance during a biopsy.

In an additional embodiment, after imaging, the gamma camera may be removed from the positioning platform and replaced with any conventional biopsy needle gun. The needle gun may be mechanically aligned based on the co-registered x-ray and gamma images, thereby allowing a more accurate biopsy to be performed.

The breast biopsy involves inserting a needle into a suspicious lesion in a breast to obtain a tissue sample. With reference to FIG. 1, the biopsy needle may be attached to an automated high-speed injection gun, which may be mounted on the positioning platform 120 that accommodated the gamma camera 114 and which now may be used to guide the placement of the biopsy needle. Once the x-ray and gamma images have been co-registered, a controller 122 then uses the co-registered images to calculate the specific position of the suspicious lesion. Once the specific position of the lesion has been determined, the needle is inserted into the breast and the injection gun is fired one or more times to remove samples from different portions of the lesion. The samples are sent to a pathologist for evaluation.

According to an embodiment of the invention, the concentration of radiotracer within the lesion of the target tissue may be determined, which may be useful in differentiation of true-positive lesions from false-positive lesions within the target tissue. This may be accomplished by acquiring multiple functional images at various angles relative to a vertical axis of the target site to be evaluated, such as a breast. For example, the gamma camera mounting gantry may allow the gamma camera to be positioned in at least three positions relative to the breast, such as at about 0°, about +15°, and about −15°.

Figure 3:
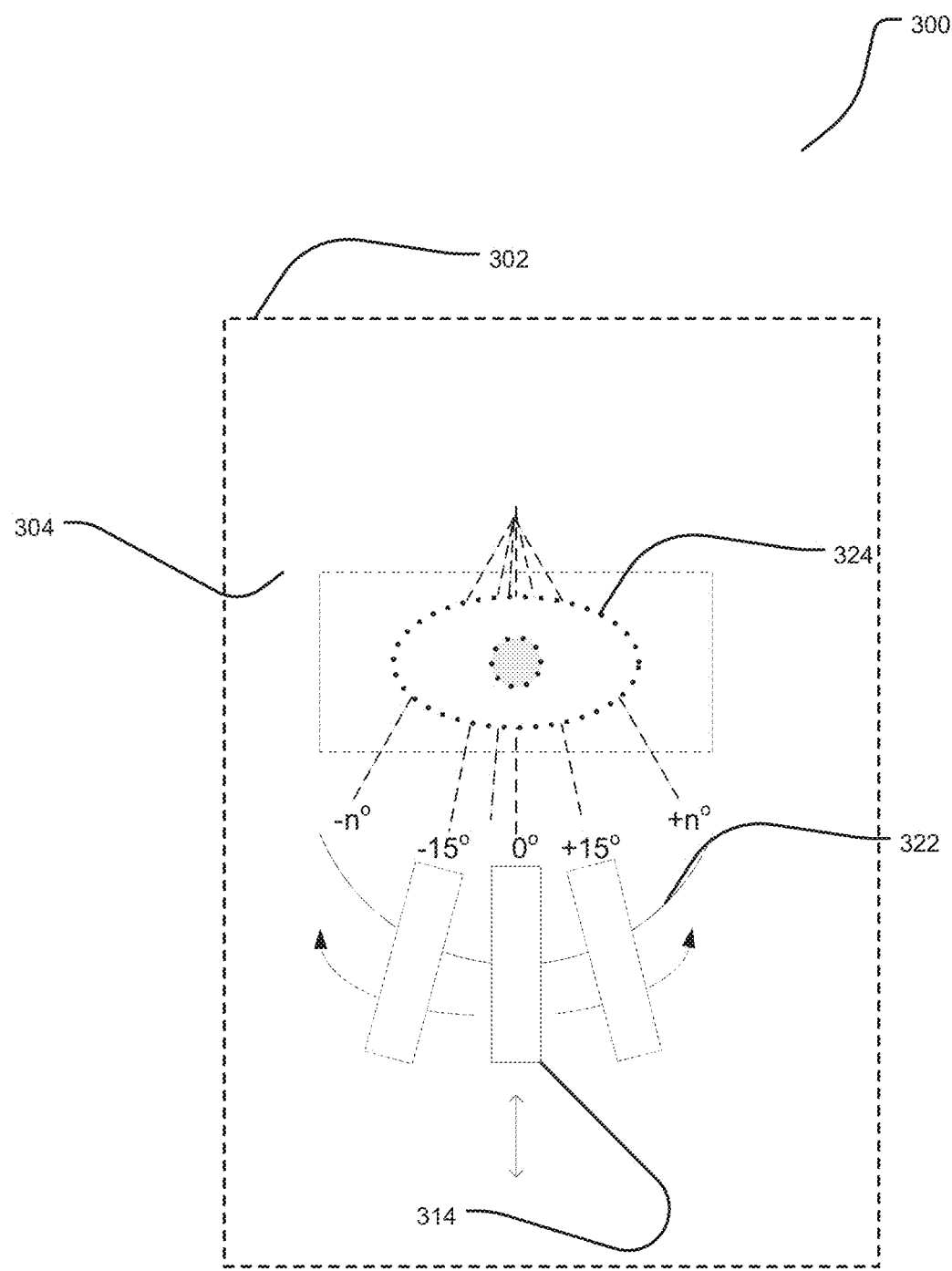
FIG. 3 provides a schematic illustration of a gamma camera mounted on a gantry allowing the gamma camera to move among a plurality of positions relative to the breast constructed according to principles of the invention.

FIG. 3 provides a schematic illustration of a gamma camera mounted on a gantry allowing the gamma camera to move among a plurality of positions relative to the breast according to principles of the invention. Referring to FIG. 3, a table 302 with an aperture 304 is shown. Breast 324 is immobilized between two compression paddles (not shown) relative to gamma camera 314, which is mounted in track 322. Gamma camera 314 is positioned at about 0° relative to the breast 324 and is capable of moving along tack 322 to various angles relative to the breast. For example, gamma camera 324 may be positioned about +15° relative to the breast or about −15° relative to the breast. Alternatively, the camera may be positioned at other angles besides about ±15°, such as angles in the range of about −45° to about ±45°.

The target tissue to be evaluated should not be construed to be limited solely to the breast, as other targets, e.g., colon, prostate, breast, thyroid, parathyroid, heart, liver, kidney, gall bladder, bladder, reproductive organs and glandular structure may be targeted for imaging. Additionally, the positions of the gamma camera should not be construed to be limited to the specific angles values related herein, but adjustments of the angle of the positions, including the number of views that may be used to calculate the radiotracer concentration within the lesion, may be made as determined by the radiologist.

Figure 4:
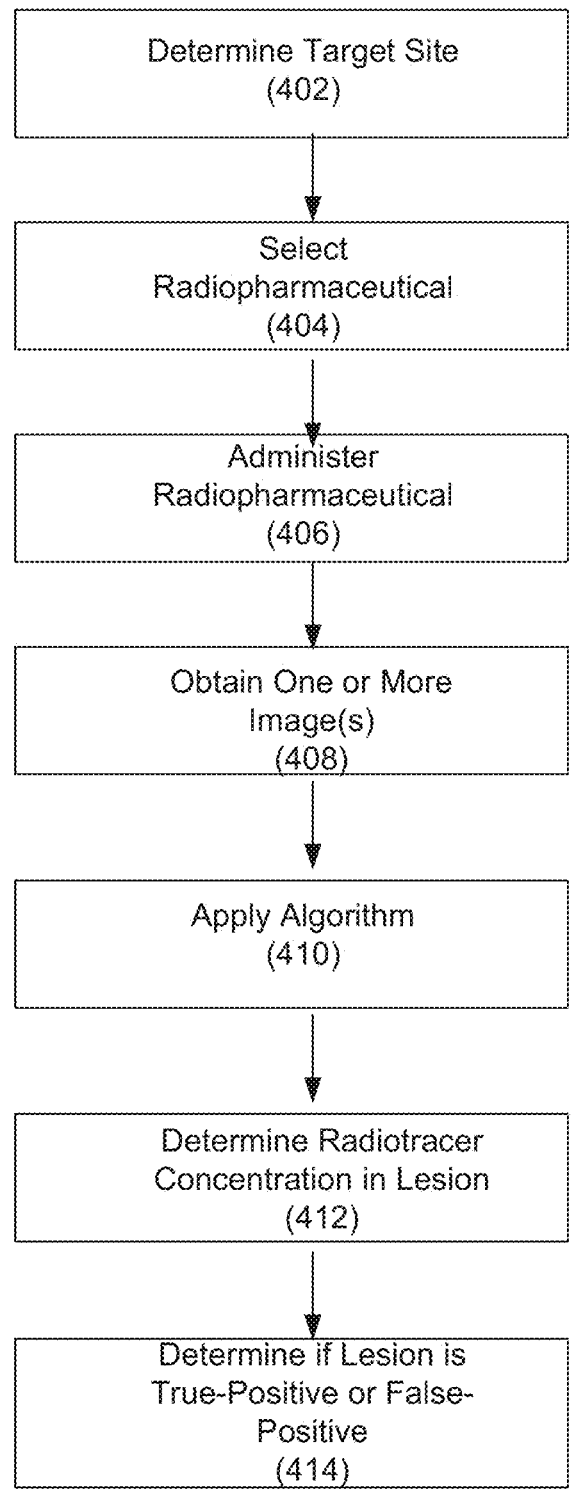
FIG. 4 is a flow chart illustrating a method for determining whether a lesion is a true-positive or a false-positive according to principles of the invention.

FIG. 4 is a flowchart illustrating a method for determining whether a lesion is a true-positive lesion or a false-positive lesion according to principles of the invention. In step 402, a physician determines the target site to be evaluated. In step 404, the appropriate radiopharmaceutical is selected based upon patient, target site and physiological process to be evaluated. In step 406, the radiopharmaceutical is administered to the patient. Subsequently, one or more functional and/or anatomical images are obtained in step 408. An algorithm is employed in step 410 and calculates the radiotracer concentration in the lesion in step 412. Finally, a physician will evaluate whether the lesion in the target site is a true-positive lesion or a false-positive lesion. The flowchart of FIG. 4 will now be described in greater detail below.

The target site to be evaluated in the patient is determined at step 402. Subsequently, a physician determines the appropriate radiopharmaceutical to use based upon the patient, the target site, and/or the physiological process desired to be evaluated at step 404. The radiopharmaceutical is introduced into the body at step 406.

The radiopharmaceutical is often bound to a compound that acts characteristically within the body and is commonly known as a tracer. In the presence of disease, a tracer will often be distributed around the body and/or processed differently. For example, the ligand methylene-diphosphonate (MDP) can be preferentially taken up by bone. By chemically attaching technetium-99m to MDP, radioactivity can be transported and attached to bone for imaging. Any increased physiological function, such as due to a fracture in the bone, may result in the appearance of a hot spot which is a focal increase radio-accumulation, or a general increase in radio-accumulation throughout the physiological system. Alternatively, some disease processes may result in the exclusion of a tracer, thereby resulting in the appearance of a cold-spot. Many different tracer complexes have been developed in order to image many different organs, glands, and physiological processes. Thus, one skilled in the art would understand the appropriate radiopharmaceutical to administered to the patient based upon the target site and/or the physiological process. Moreover, as described above, other radiopharmaceuticals may be used for identifying lesions in the breast. The radiopharmaceuticals may include, for example, Technetium-99m, iodine-123, iodine 131, thallium-201, gallium-67, fluroine-18, xenon-133, krypton-81m, and Technegas®.

The radiopharmaceutical may be administered by intravenous injection, subcutaneous injection, intrasynovial injection, inhalation, ingestion, intrathecal injection, and topical application. For intravenous injection, the radiopharmaceutical is injected in the vein. Many different types of evaluations may be accomplished using this method, such as the technetium-99m-MDP bone scan. With subcutaneous injection, the radiopharmaceutical is injected under the skin, and may be used when investigating the lymphatic system. Moreover, intrasynovial injection may be used when examining a joint space, such as knee joint. In this method, a radiopharmaceutical, such as yttrium-90, is injected directly into the joint space. Some radiopharmaceuticals may be inhaled by the patient, typically when investigating the lungs. For example, gases such as krypton-81m, and aerosols, including technetium-99m, may be administered to the patient. Additionally, the radiopharmaceutical may be administered to the patient by intrathecal injection. With this method, the radiopharmaceutical in injected into the subarachnoid space, usually via lumbar puncture and is generally used when investigating the cerebrospinal fluid (CSF) circulation or for detecting CSF leaks. The radiopharmaceutical also may be administered topically to the patient. Using this method, the radiopharmaceutical is directly delivered to the area to be investigated, such as the administration of technetium-99m eyedrops to investigate the tear-duct flow.

Following administration of the appropriate radiopharmaceutical to the patient, the radiation emitted by the patient may be detected at step 408, using an imager, such as a gamma camera, such that one or more functional images may be obtained. One or more x-ray images may also be obtained. According to an embodiment of the invention, the gamma camera mounting gantry may allow the gamma camera to be positioned in multiple positions relative to the target site to be evaluated. By way of example, three positions may be located on a stereotactic arc of about 0°, about +15, and about −15°. FIG. 3 described above, for example, provides a schematic illustration of a system 300 having at least one gamma 314 camera capable of positioning in a plurality of positions relative to the breast 324. As illustrated in FIG. 3, the system 300 includes a table 302 having an aperture 304. A patient's breast 324 is placed within the aperture 324. In this placement, one or more cameras may be used at varying positions along the track 322 relative to the breast 324. This arch may allow the stereotactic localization to be completed with the gamma images alone.

Once the gamma images have been obtained, an algorithm may be applied to the gamma image data at step 410. For example, by using a back projection technique from each of the three views, a gross estimation of lesion volume may be made using this data along with the breast compression thickness, resolution and attenuation corrections, and detector quantum efficiency.

At step 412, the absolute concentration of radiotracer in the lesion is calculated after obtaining at least three projections (e.g., at −15°, 0°, and)+15° of the lesion. This dataset allows the z-coordinate to be calculated and for the lesion dimensions of height, width, and length to be measured in the three projections. From these measurements, a rough lesion volume is calculated. Next, using the 0° image, a ROI for the lesion is drawn and the total counts in the region is measured for detector sensitivity, impact of detector resolution, and attenuation, the absolute activity for the region is calculated (mCi). After the background noise is subtracted, the remaining value is corrected volume resulting in mCi/ml or some other activity per volume value. This value may be useful in differentiating true-positive from false-positive cases at step 414. While a method according to principles of the invention has been described in FIG. 4, it is understood that additional steps may be added to the method, steps may be omitted from the method and/or steps may be performed in a different order without departing from the scope of the invention.

Moreover, by incorporating dynamic radiotracer uptake quantification, radiotracer wash-in may be analyzed for differentiation. Both of these methods may allow more detailed studies of radiotracer pharmacokinetics than previous systems. Although stereotactic biopsy may be possible with these three views alone, the gamma detector may be mounted on the arch using a motorized system allowing images to be obtained anywhere along the arch. This precision motor controlled movement would make the system capable of limited angle tomographic imaging. If the x-ray system is enabled to do tomographic imaging as well, this would allow fusion between the tomographic modalities.

According to an embodiment of the invention, a system employs only one gamma detector head. Since three views are required for localization and each of these views requires several minutes, alternative embodiments may employ multiple heads to reduce study time while allowing the radiotracer wash in to be recorded from multiple angles. According to an embodiment of the invention, if a system employs two gamma detector heads, one could be fixed at an about +15° view while the other could rotate between an about −15° view and an about 0° view. A triple gamma detector head system would allow detectors to be mounted in all three stereotactic positions simultaneously for an even greater study time reduction. Other configurations may also be used.

Therefore, according to embodiment of the invention, a two or three detector head nuclear medicine imaging system may be employed to provide images simultaneously from multiple angles, thereby reducing the stereotactic imaging time compared to a single detector head system. In addition, the system may allow dynamic radiotracer wash-in studies to be simultaneously viewed from multiple angles.

Figure 5:
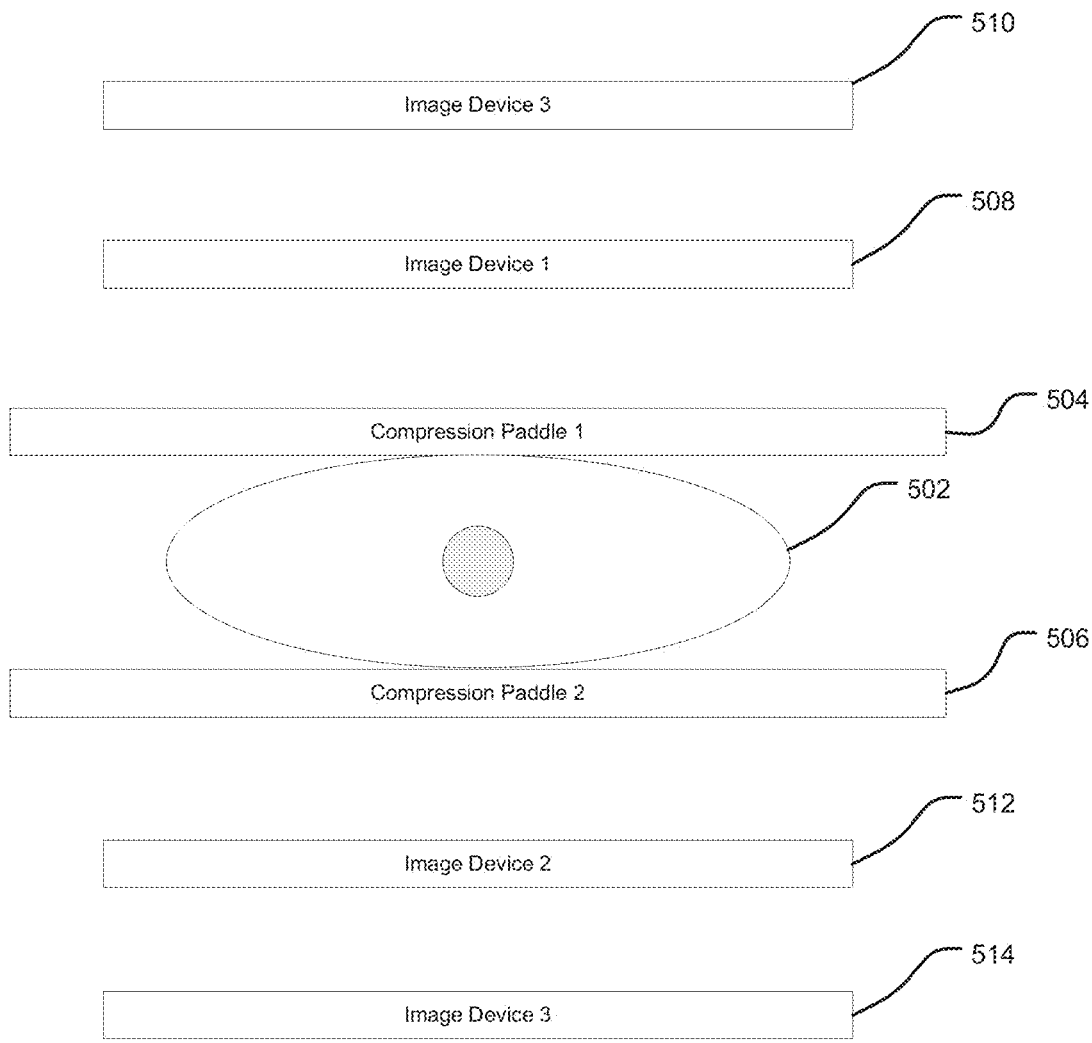
FIG. 5 is a schematic illustration of an opposed dual head detector apparatus constructed according to principles of the invention.

According to an embodiment of the invention, two opposed gamma camera images of radiopharmaceutical uptake within a target site, such as the breast, may be utilized to determine the X, Y, and Z coordinates of a lesion for the purpose of biopsy. For example, a detector or detectors are positioned on either side of an immobilized breast. FIG. 5 is a schematic illustration of an opposed dual head detector apparatus according to principles of the invention. The apparatus includes a breast 502 immobilized between compression paddle 504 and compression paddle 506. Imaging device 508, imaging device 512, imaging device 510, and imaging device 514 are positioned to obtain images of breast 502. By way of example, imaging device 508 may be an x-ray generator, imaging device 512 may be an x-ray detector, imaging device 510 may be a gamma camera and imaging device 514 may be a gamma camera.

The imaging system described in the embodiment of FIG. 5 should not be construed to be limited to this configuration, but may be configured in any number of ways. For example, the system may only include imaging device 508, which may be an x-ray generator, and imaging device 506, which may be an x-ray detector. Alternatively, imaging device 508 may be a gamma camera and imaging device 510 may be an x-ray generator and imaging device 514 may be an x-ray detector.

Lesion location may be determined in one or both acquired images. The Z location may be calculated by comparing the signal of lesion in the acquired images, such as by using comparative signal intensity and spatial resolution. For example, this may be done by comparing functional images from one or more gamma cameras. Since it can be assumed that the detector heads are looking at the same foci, a lesion located equidistant from both detector heads would yield very similar signal characteristics. If the lesion is closer to one detector head than to the other, attenuation and resolution changes result in a change in signal for both detector heads. By measuring and modeling these changes, the Z location of the lesion may be determined. Although this lesion localization methodology has been described above using gamma cameras, it is understood that other types of imaging may be used.

Using the lesion X, Y and Z location from the method discussed above, the sensitivity of the detector, the breast compression thickness and a simple attenuation model, the specific activity for the lesion volume can be determined. According to an embodiment of the invention, a method for determining specific activity may begin with determining the height (Y coordinate) and width (X coordinate) of the mass using the acquired images. The thickness (Z coordinate), is assumed to be the mean of the height and width. Based on these parameters, the volume of the lesion is calculated. A region of interest (ROI) is drawn around the lesion and the number of counts in the region is determined. The same sized ROI is drawn in the background and number of counts is determined. The number of counts in the background is divided by the area of the ROI in mm and then by the breast thickness in mm, where the resulting value is expressed as (counts per $mm^3$). The lesion height is subtracted from the total breast thickness, and the result is the height of background tissue above and below the lesion in the lesion ROI. The background tissue height is multiplied by the value of the background counts divided by the area ROI. The result is the number of non-lesion counts/$mm^3$ in the lesion ROI. The number of non-lesion counts is subtracted from the counts/$mm^3$ in the lesion ROI, where the result is the number of counts from the area of the lesion. The number of counts from the area of the lesion is divided by the height of the lesion. This result is the counts per volume. The counts per volume are multiplied by a correction factor accounting for the efficiency of the detector system. This final result is the concentration value. This concentration value (mCi/$mm^3$) is a better measure of lesion uptake than contrast (the current method for evaluation) which is dependent on lesion volume. Other methods may also be used.

The gantry mount embodiment described previously may include a gantry with a breast immobilization device and one or more gamma cameras for imaging. The gamma camera or cameras are capable of acquiring opposed views of the immobilized breast. The gamma camera or cameras may be mounted such that they may be moved into an imaging position around the breast or swung out of the way to allow access to the breast for biopsy. The immobilization device may be designed to allow a biopsy to be conducted through the walls of the device or through provided access panels.

Figure 6A:
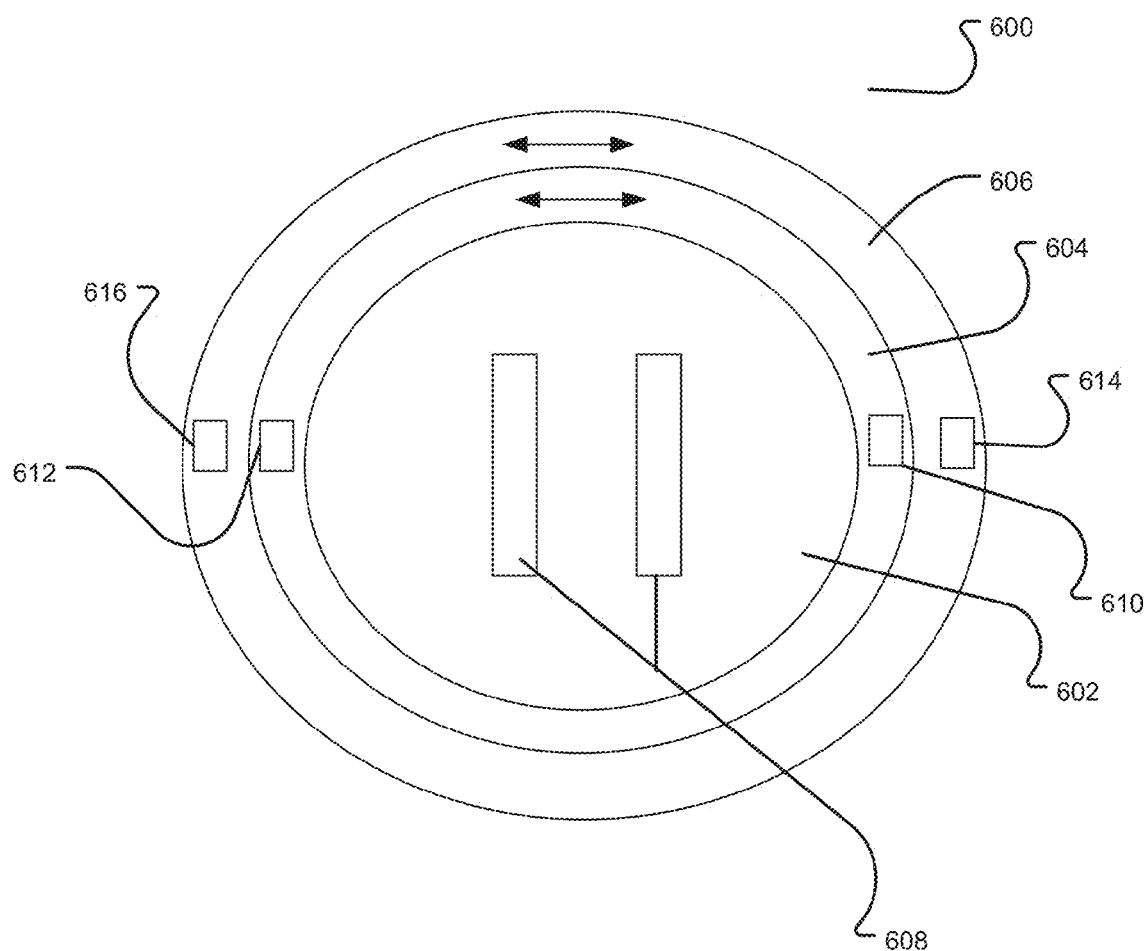
FIG. 6A provides a schematic illustration of a top view of a moveable mounting gantry for use in the system constructed according to principles of the invention.
Figure 6B:
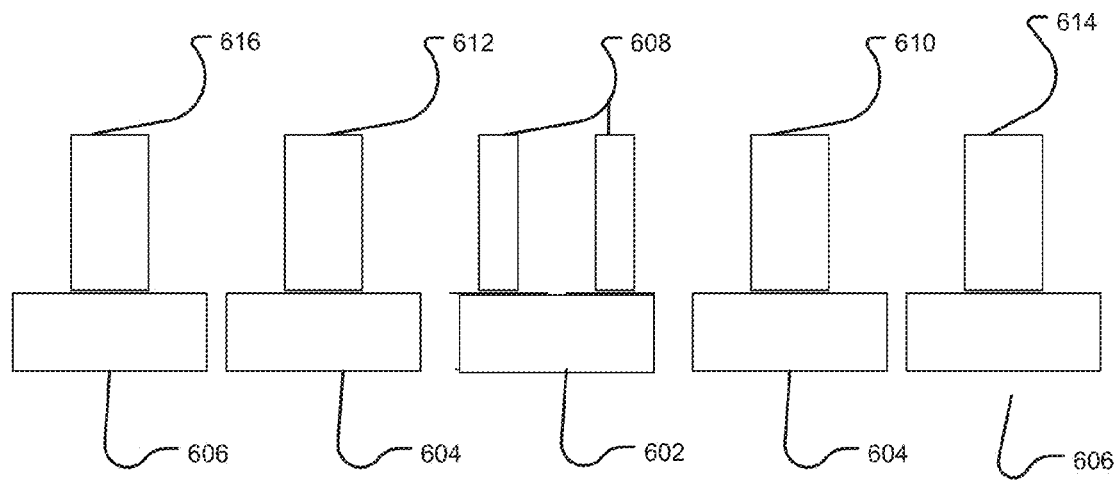
FIG. 6B provides a schematic illustration of a cut-away view of the mounting gantry of FIG. 6A.

Alternatively, the gamma camera may be mounted on a gantry having concentric sliding rings. FIG. 6A provides a schematic illustration of a top view of a moveable mounting gantry according to principles of the invention. FIG. 6B provides a schematic illustration of cut-away views of the mounting gantry of FIG. 6B. A system 600 includes a stationary mount 602, an inner concentric sliding ring 604, and an outer concentric sliding ring 606. Compression paddles 608 are moveably mounted on stationary mount 602. An x-ray generator 610 is mounted on the inner concentric ring 604, and an x-ray detector 612 is mounted on the inner sliding ring 604. A gamma camera 614 is mounted on the outer concentric sliding ring 606 and a gamma camera 616 is mounted on the outer concentric sliding ring 606. FIGS. 6A and 6B are exemplary and should not be construed to be limit to this particular configuration.

The concentric ring 604 permits the x-ray detector 612 and the x-ray generator 610 to move relative to the target while still maintaining the alignment between the x-ray generator 610 and the x-ray detector 612. Further, concentric ring 606 permits the gamma cameras 614 and 616 to move relative to the target while still maintaining the alignment between the gamma cameras 614 and 616.

The gantry system 600 may be capable of accommodating the compression paddles 608, gamma cameras 614 and 616, x-ray detectors 612, or x-ray generators 610. Moreover, if the rings 604, 606 are equipped with compression paddles 608, the paddles 608 can slide in and out to accommodate breast size variation as conventional paddles, such as with set screws, stepper motor, etc. (not shown). Alternatively, the compression paddles 608 may be rigidly fixed to the rings 604, 606 and allow the rings 604, 606 to have an adjustable array of radii. The concentric sliding rings 604, 606 may be mounted to a "wheel in place" gantry which would not interfere with mammographic or stereotactic equipment. The gantry may move in front of the patient for imaging and then be simply wheeled away when the imaging is completed.

Of the available radiotracers, the invention may compatible for use with, but not limited to imaging abscess and infection by using gallium citrate Ga 67, and indium In 111 oxyquinoline; biliary tract blockage using technetium Tc 99m disofenin, technetium Tc 99m lidofenin, and technetium Tc 99m mebrofenin; blood volume studies using radioiodinated Albumin, sodium chromate Cr 51; blood vessel diseases using sodium pertechnetate Tc 99m; blood vessel diseases of the brain using ammonia N 13, iofetamine I 123, technetium Tc 99m bicisate, technetium Tc 99m exametazime, and xenon Xe 133; bone diseases using sodium fluoride F 18, technetium Tc 99m medronate, technetium Tc 99m oxidronate, technetium Tc 99m pyrophosphate, and technetium Tc 99m (pyro- and trimeta-) phosphates; bone marrow diseases using sodium chromate Cr 51, technetium Tc 99m albumin colloid, and technetium Tc 99m sulfur colloid; brain diseases and tumors using fludeoxyglucose F 18, indium In 111 pentetreotide, iofetamine I 123, sodium pertechnetate Tc 99m, technetium Tc 99m exametazime, technetium Tc 99m gluceptate, and technetium Tc 99m pentetate; cancer and tumors using fludeoxyglucose F 18, gallium citrate Ga 67, indium In 111 pentetreotide, indium In 111 iatumomab pendetide, methionine C 11, radioiodinated iobenguane, sodium fluoride F 18, technetium Tc 99m arcitumomab, and technetium Tc 99m nofetumomab merpentan; colorectal disease using technetium Tc 99m arcitumomab; disorders of iron metabolism and absorption using ferrous citrate Fe 59; heart disease using ammonia N 13, fludeoxyglucose F 18, rubidium Rb 82, sodium pertechnetate Tc 99m, technetium Tc 99m albumin, technetium Tc 99m sestamibi, technetium Tc 99m teboroxime, technetium Tc 99m tetrofosmin, and thallous chloride Tl 201; heart muscle damage (infarct) using ammonia N 13, fludeoxyglucose F 18, rubidium Rb 82, technetium Tc 99m pyrophosphate, technetium Tc 99m (pyro- and trimeta-) phosphates, technetium Tc 99m sestamibi, technetium Tc 99m teboroxime, technetium Tc 99m tetrofosmin, and thallous chloride Tl 201; impaired flow of cerebrospinal fluid in brain using indium In 111 pentetate; kidney diseases using iodohippurate sodium I 123, iodohippurate sodium I 131, iothalamate sodium I 125, technetium Tc 99m gluceptate, technetium Tc 99m mertiatide, technetium Tc 99m pentetate, and technetium Tc 99m succimer; liver diseases using ammonia N 13, fludeoxyglucose F 18, technetium Tc 99m albumin colloid, technetium Tc 99m disofenin, technetium Tc 99m lidofenin, technetium Tc 99m mebrofenin, and technetium Tc 99m sulfur colloid; lung diseases using krypton Kr 81m, technetium Tc 99m albumin aggregated, technetium Tc 99m pentetate, and xenon Xe 127, xenon Xe 133; parathyroid diseases and parathyroid cancer using technetium Tc 99m sestamibi, thallous chloride Tl 201; pernicious anemia and improper absorption of vitamin $B_{12}$ from intestines using cyanocobalamin Co 57; red blood cell diseases using sodium chromate Cr 51; salivary gland diseases using sodium pertechnetate Tc 99m; spleen diseases using sodium chromate Cr 51, technetium Tc 99m albumin colloid, and technetium Tc 99m sulfur colloid; stomach and intestinal bleeding using sodium chromate Cr 51, sodium pertechnetate Tc 99m, technetium Tc 99m (pyro- and trimeta-) phosphates, and technetium Tc 99m sulfur colloid; stomach disorders using technetium Tc 99m sulfur colloid; tear duct blockage using sodium pertechnetate Tc 99m; thyroid diseases and thyroid cancer using fludeoxyglucose F 18, indium In 111 pentetreotide, radioiodinated iobenguane, sodium iodide I 123, sodium iodide I 131, sodium pertechnetate Tc 99m, and technetium Tc 99m sestamibi; and urinary bladder diseases using sodium pertechnetate Tc 99m.

Without further elaboration, it is believed that one skilled in the art, using the preceding description, can utilize the invention to the fullest extent. The following examples are illustrative only, and not limiting of the disclosure in any way whatsoever.

EXAMPLES

Figure 7:
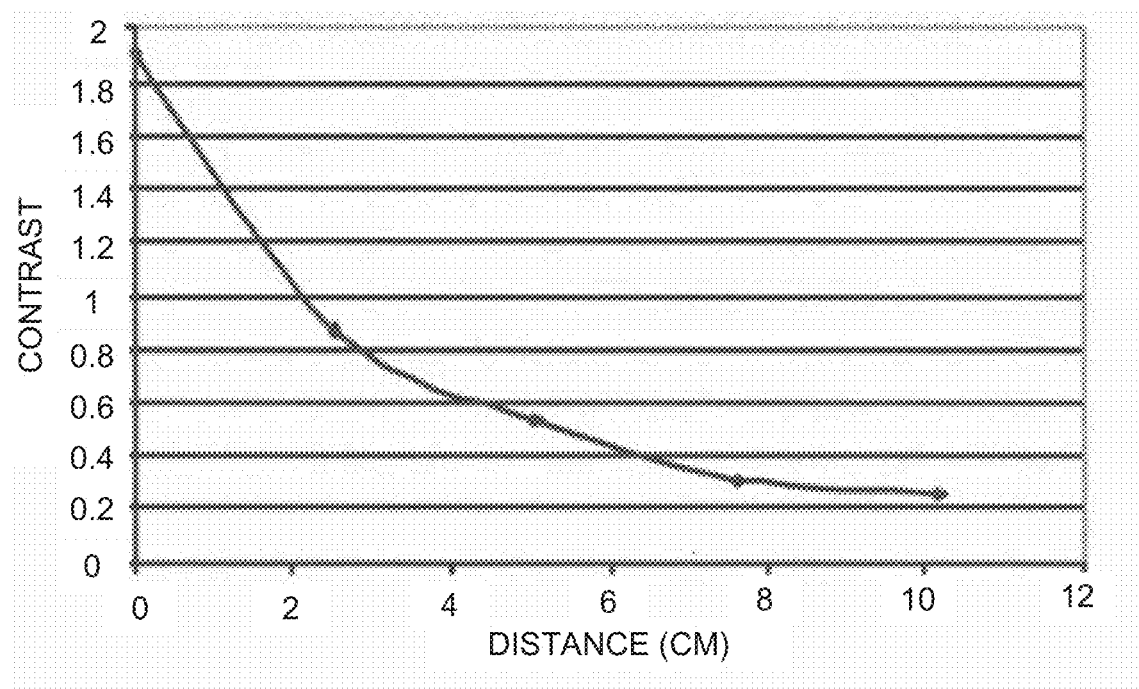
FIG. 7 is a graph illustrating the lesion contrast as a function of depth in a phantom for a 1 cm diameter spherical lesion phantom in a 10 cm thick breast phantom with a 6:1 lesion-to-background ration.

Phantom studies have indicated that two techniques can substantially enhance lesion contrast and signal-to-noise ratios. First of all, applying breast compression reduces the cross-sectional thickness of breast tissue which improves lesion contrast. Secondly, the minimization of lesion-to-detector distance dramatically improves lesion signal by reducing signal losses due to attenuation and decreased collimator resolution. FIG. 7 is a graph illustrating the lesion contrast as a function of depth in a phantom for a 1 cm diameter spherical lesion phantom in a 10 cm thick breast phantom with a 6:1 lesion-to-background ratio. Specifically, the contract reduces as distance increases. Given these two observations, a system comprised of two opposed detector heads compressing the breast was provided that yielded improved visualization of breast lesions. To evaluate this concept, several studies with compressed breast (e.g., a mean thickness of about 6 cm+/−about 1.5 cm) and lesion phantoms containing an about 6:1 lesion-to-background tracer concentration ratio were conducted. The results of these experiments indicated that lesions with a diameter of about 8 mm or greater were easily visible in both detectors while lesions of about 5 mm and smaller were difficult to detect, especially if located near the center of the breast. For these centrally located lesions, some level of lesion signal was often present in both detectors, but not truly distinguishable above noise. The following specific examples describe a series of experiments that were used to evaluate the two image processing techniques of geometric mean and contrast mapping. In addition, a comparison between this dual detector approach to single gamma and positron tomographic techniques was conducted in specific examples immediately below.

In the specific examples immediately below, gamma camera prototypes were based on an array of compact Hamamatsu R7600-00-C8 position sensitive photomultiplier tubes (PSPMTs). The PSPMT array was optically coupled to a high quality pixellated NaI(Tl) array manufactured by Bicron Corporation (Milford, N.H.). The scintillator array was a matrix of about 3 mm×about 3 mm×about 6 mm crystals encapsulated in a compact housing with about a 5 mm thick glass window. Each NaI(Tl) pixel element was separated by about 0.3 mm septa made of diffusing white epoxy. The average system energy resolution was about 17.5% FWHM at about 140 keV.

The system was fitted to have a high resolution or a high efficiency, depending on the specific requirements of the experiment, as shown in Table 1 immediately below.

TABLE 1

|  | Hole Diameter | Height | Septa |
|---|---|---|---|
| High Resolution | 1.778 | 19.99 | 0.305 |
| High Efficiency | 1.397 | 27.000 | 0.203 |

Figure 8:
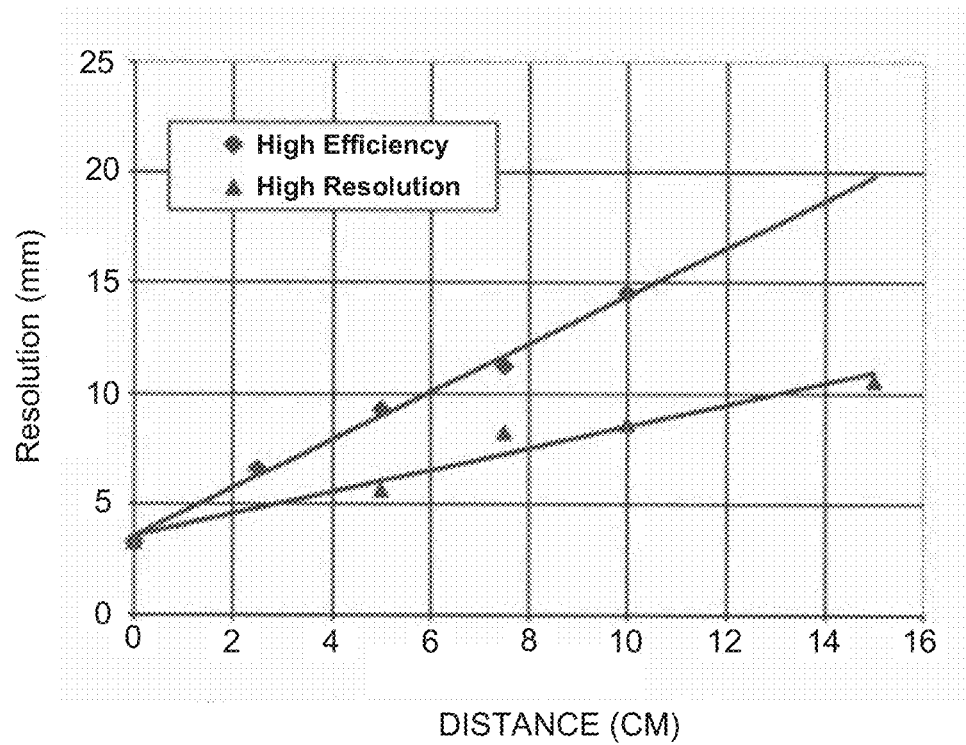
FIG. 8 is a graph illustrating system resolution with increasing source to detector distance for both high resolution and high efficiency collimators.

For example, all SPECT studies were conducted with the high resolution collimator to preserve study resolution at greater distances since the center-of-rotation to collimator distance was about 10 cm. FIG. 8 is a graph illustrating system resolution with increasing source to detector distance for both the high resolution and high efficiency collimators.

Specific Example 1

This example utilized an about 5 cm thick plastic breast phantom with an about 6 mm hollow sphere lesion located near the center of the breast phantom. The breast volume was filled with a Tc99m solution with a concentration of about 0.33 µCi/ml and the lesion volume concentration was about 1.98 µCi/ml. Two opposing 10 minute acquisitions were obtained. A pair of Co-57 point sources was taped to the edge of the phantom to aid in alignment of the opposing views.

The phantom was then emptied and refilled with F-18 for imaging with a dedicated small field-of-view positron breast imaging system, (PEM). The breast volume contained a concentration of about 0.08 µCi/ml and the lesion concentration was about 6:1 over that of the breast. Imaging was conducted for about 20 minutes and image reconstruction was completed using a classical back-projection tomography techniques.

Figure 9A:
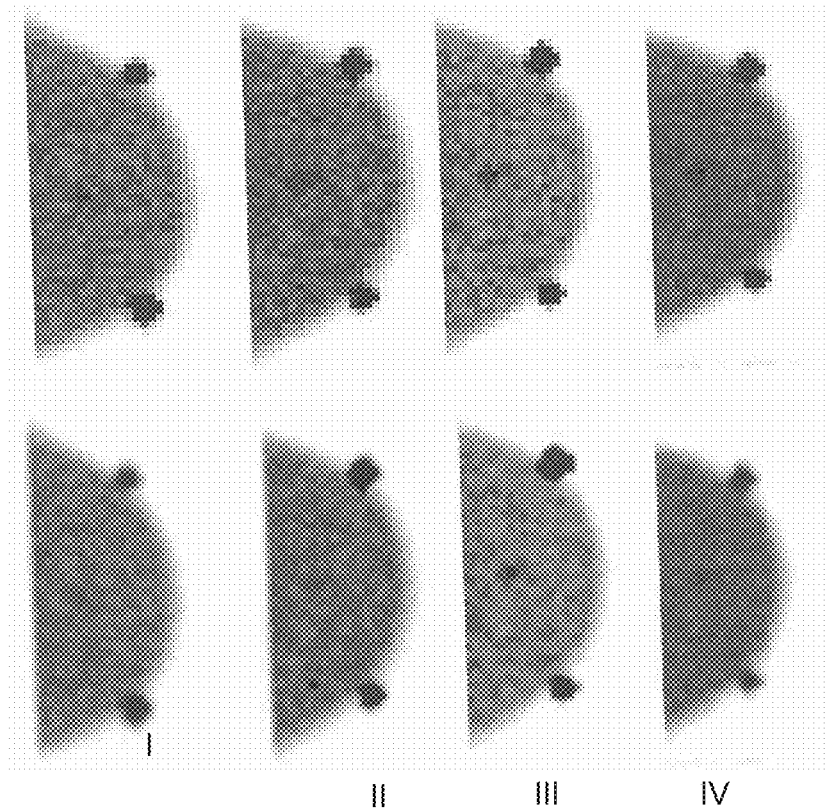
FIG. 9A shows phantom images from the single gamma camera system in an example using principles of the invention.

FIG. 9A shows phantom images from the single gamma camera system, with the resulting images from the $Tc^{99}$ single gamma case. The planar images from the two detector positions and the resulting image from both fusion techniques were shown in unsmoothed (see Panel I) and smoothed sets (see Panel II). The Contrast Map images (see Panel III) and the Geometric Mean images (see Panel IV) are also shown. About a 3×3 mean smoothing kernel was used for image processing.

Figure 9B:
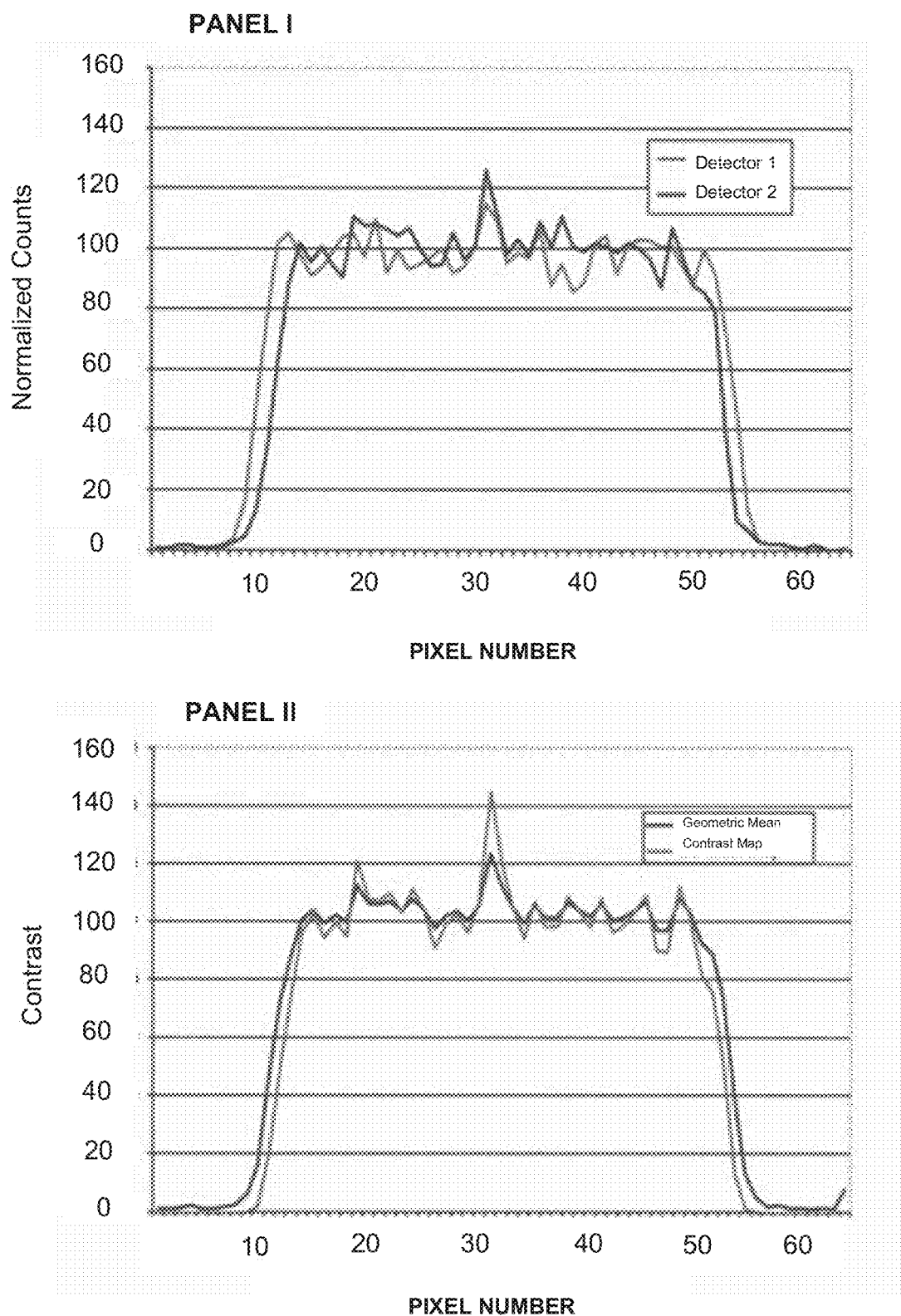
FIG. 9B show the lineout graphs demonstrating the lesion contrast in each of the detector images and in each of the image fusion techniques of the example in FIG. 9A.

Vertical lineouts through the center of the lesion are shown in FIG. 9B. In order to facilitate direct comparison, the lineout data for each of the detectors, as shown in Panel I, was normalized such that the average background is equal to about 100. The contrast map technique and the geometric mean technique are both illustrated in Panel II, where the contrast map technique provided the best contrast in this comparison. The noise level for both of the processed images was calculated by propagating the noise level from each detector images (square root of the mean pixel value) through the image processing algorithm. The lesion contrast and S:N for each image is listed in Table 2, immediately below.

TABLE 2

|  | Detector 1 | Detector 2 | Contrast Map | Geometric Mean |
|---|---|---|---|---|
| Contrast | 0.14 | 0.26 | 0.45 | 0.20 |
| S:N | 3.1 | 5.6 | 3.5 | 2.5 |

The contrast map technique demonstrated a better S:N ratio than the geometric mean image, but poorer than that of the image from detector 2. Given the poor performance of the geometric mean method, it was not calculated for the second experiment presented in Example 2, infra.

Figure 10A:
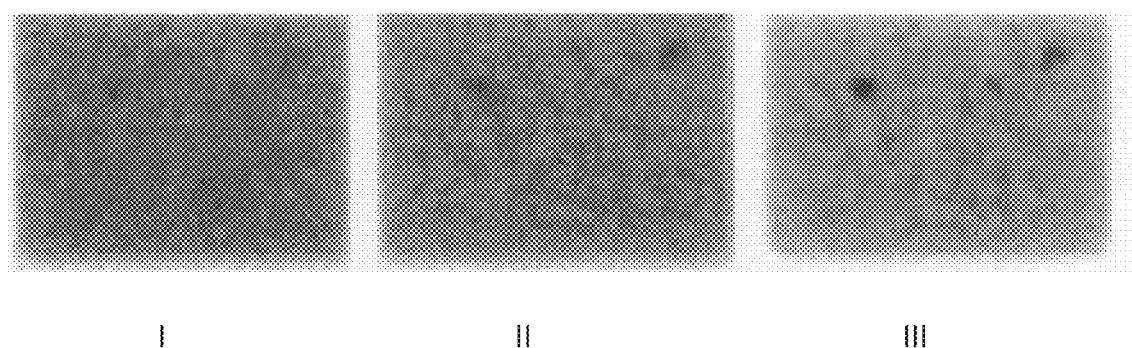
FIG. 10A shows 10 minute static acquisitions from different detector head positions and the contrast map images in an example using principles of the invention.

FIG. 10A shows 10 minute static acquisitions from different detector head positions and the contrast map image in an example using principles of the invention. The resulting images from the PEM system. The reconstruction plane was at the center of the lesion and was displayed as unsmoothed in Panel I and smoothed in Panel II. The phantom background was prepared to simulate an average expected FDG breast tissue uptake level of about 0.092 mCi/cc. An acceptance angle of about 20° was used for the image reconstruction.

Figure 11A:
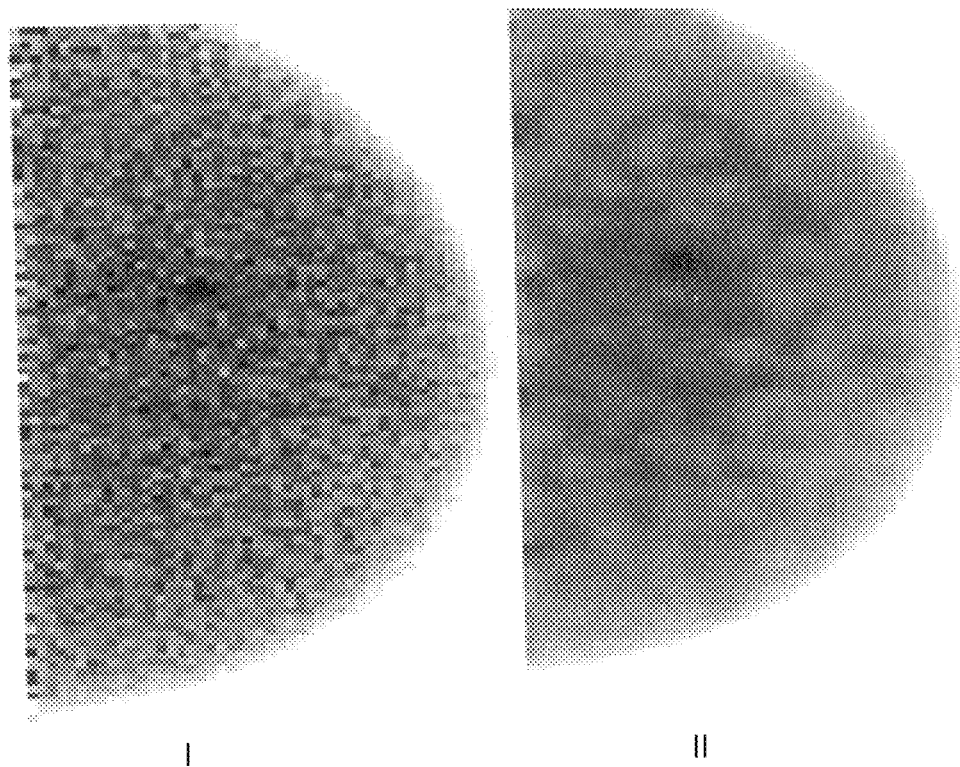
FIG. 11A shows unsmoothed and smoothed images from the PEM system using a phantom filled with F-18 (6:1 lesion-to-phantom concentration ratio) in an example using principles of the invention.
Figure 11B:
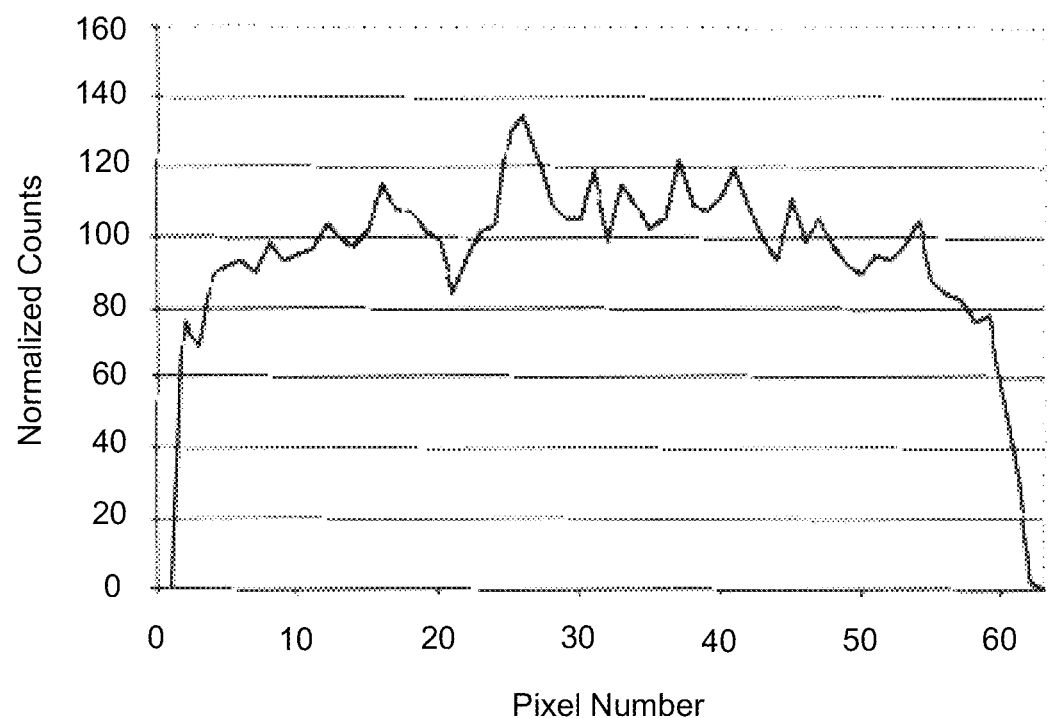
FIG. 11B shows the vertical lineout graph through the lesion from the unsmoothed PEM image of the example of FIG. 11A.

FIG. 11A shows an unsmoothed (Panel I) and smoothed (Panel II) images from PEM system using a phantom filled with F-18 (6:1 lesion-to-phantom concentration ration). FIG. 11B shows a vertical lineout through the lesion from the unsmoothed PEM image from FIG. 11A. this lineout through the center of the lesion clearly demonstrating the lesion signal. Table 3, shown immediately below, provides the contrast and S:N ratio for the resulting PEM image. The contrast measured for the contrast map technique (Table 2) is slightly better than that of the PEM system (Table 3), but the higher sensitivity of the PEM system provided higher imaging statistics and therefore an improved S:N.

TABLE 3

|  | PEM Image |
|---|---|
| Contrast | 0.37 |
| S:N | 4.98 |

Specific Example 2

In the second experiment, about a 4.5 cm thick compressed breast phantom with a Tc99m concentration of 0.9

μCi/ml was prepared containing three lesions (two of about 8 mm diameter and one of about 6 mm diameter) containing an about 6:1 concentration over background and two 10 minute static acquisitions were obtained. A SPECT acquisition was performed with the same lesions and background solution transferred to a cylindrical ("uncompressed") phantom with a diameter of about 9.25 cm. The SPECT acquisition angular sampling was set at about 3 degrees/step and the imaging time was set at about 30 seconds/frame. These parameters were selected to simulate about a 40 minute patient imaging time with a dual head system. Image reconstruction was obtained using a filtered back-projection technique.

In the planar imaging case, both the about 8 mm lesions and the about 6 mm lesion were visible in detector position 1 (Panel I of FIG. 10A). However, the about 6 mm lesion was not seen from detector position 2 (Panel II of FIG. 10A). These results demonstrated that the impact of collimator to lesion distance on lesion signal as the lesion was located about 1 cm from the collimator in the detector position 1 and about 4 cm from the detector position 2. In addition, the about 6 mm lesion signal was clearly enhanced in the contrast map image of Panel III in FIG. 10A.

Figure 10B:
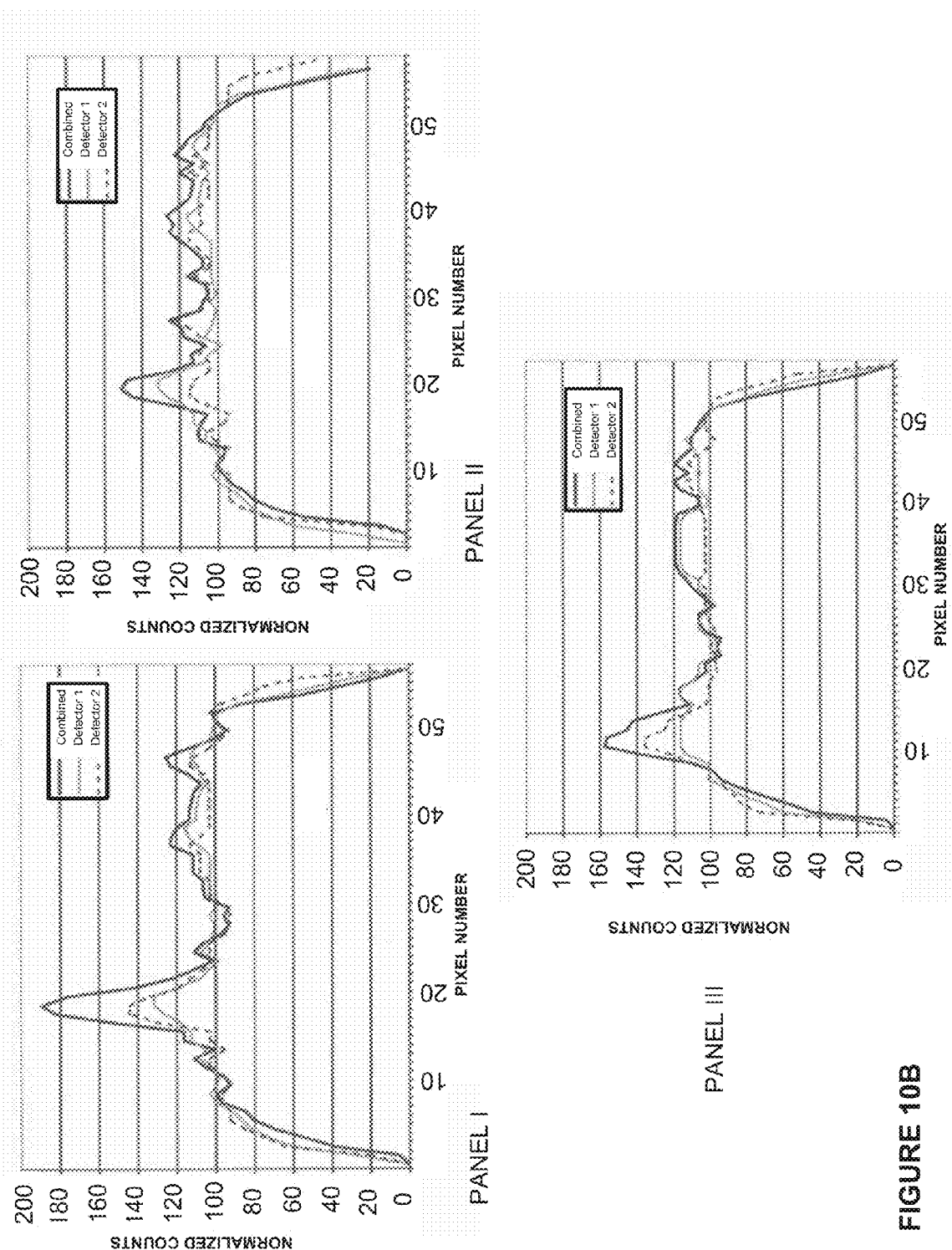
FIG. 10B shows the lineout graphs demonstrating the lesion contrast for each of the three images of the example of FIG. 10A.

Vertical lineouts through each of the three lesions are shown in Panels I, II and II of FIG. 10B. Each normalized graph displayed the lineouts from the planar images and the processed image. In FIG. 10B, Panel I corresponds to Panel I of FIG. 10A, Panel II corresponds to Panel II of FIG. 10A, and Panel III corresponds to Panel III of FIG. 10A. The contrast for all lesions was enhanced in the contrast map image. In addition, S:N and contrast ratios were calculated for the contrast map image and are shown in Table 3 for reference.

Figure 12A:
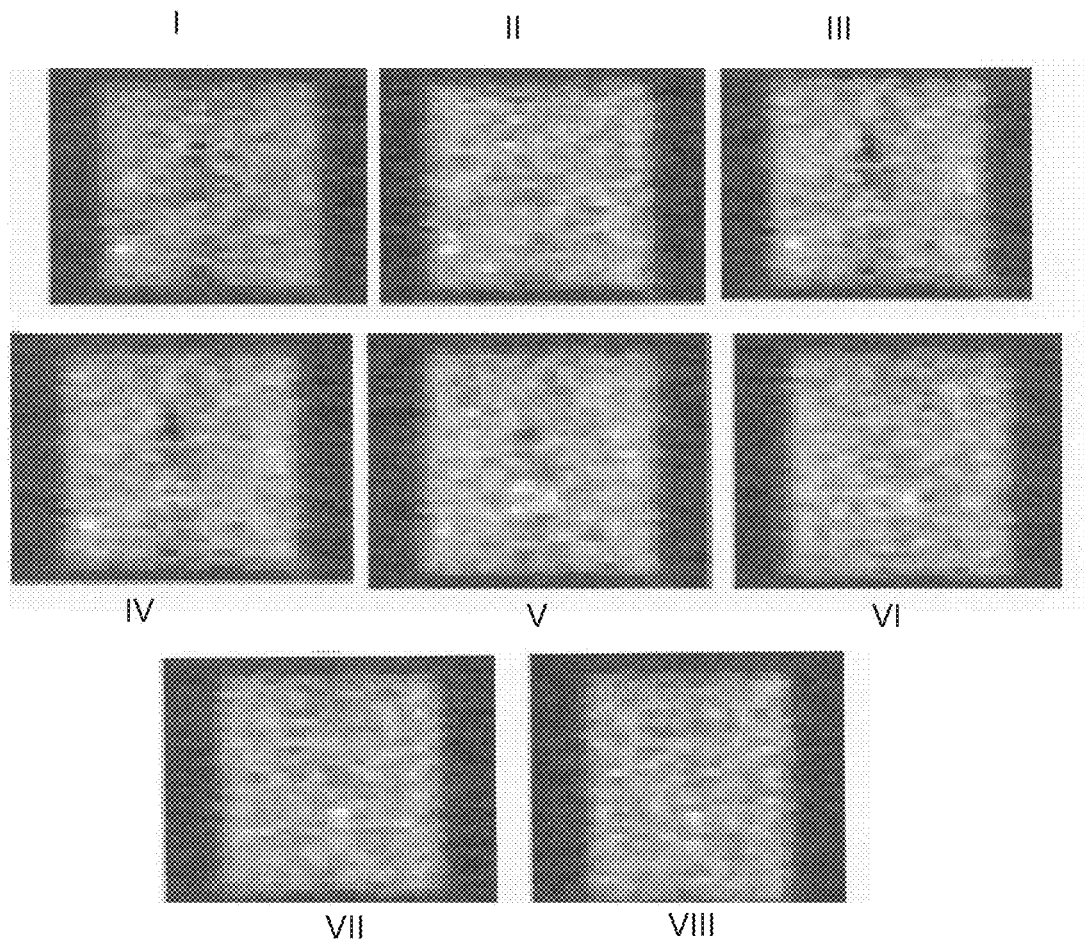
FIG. 12A shows the SPECT reconstruction of the cylinder phantom in an example using principles of the invention.
Figure 12B:
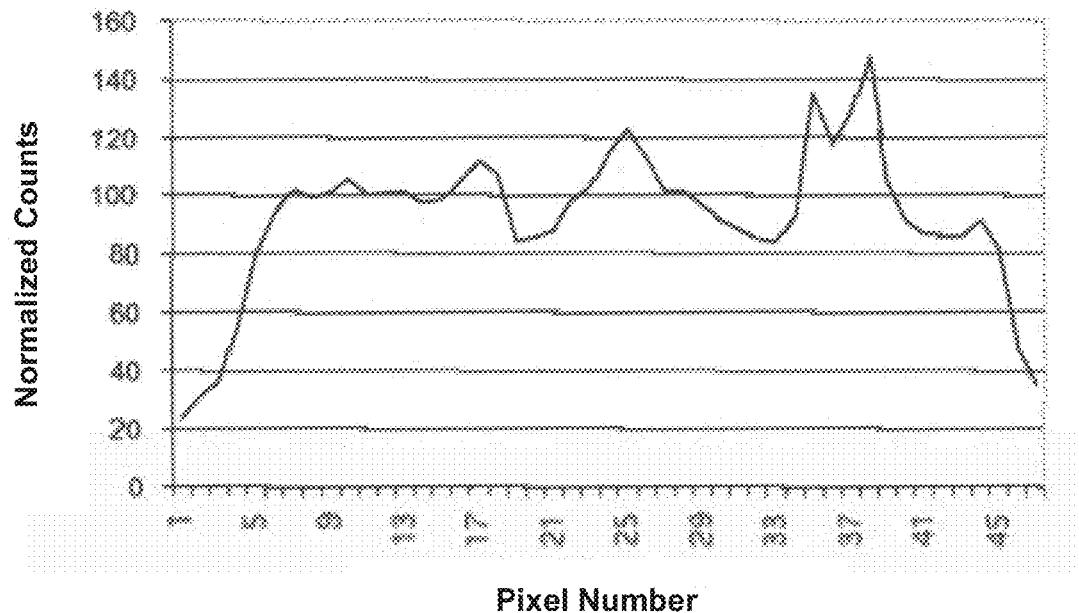
FIG. 12B provides the lineout graphs for each of the 8 mm lesions seen in slices 2 and 7 respectively of the example of FIG. 12A.
Figure 12B:
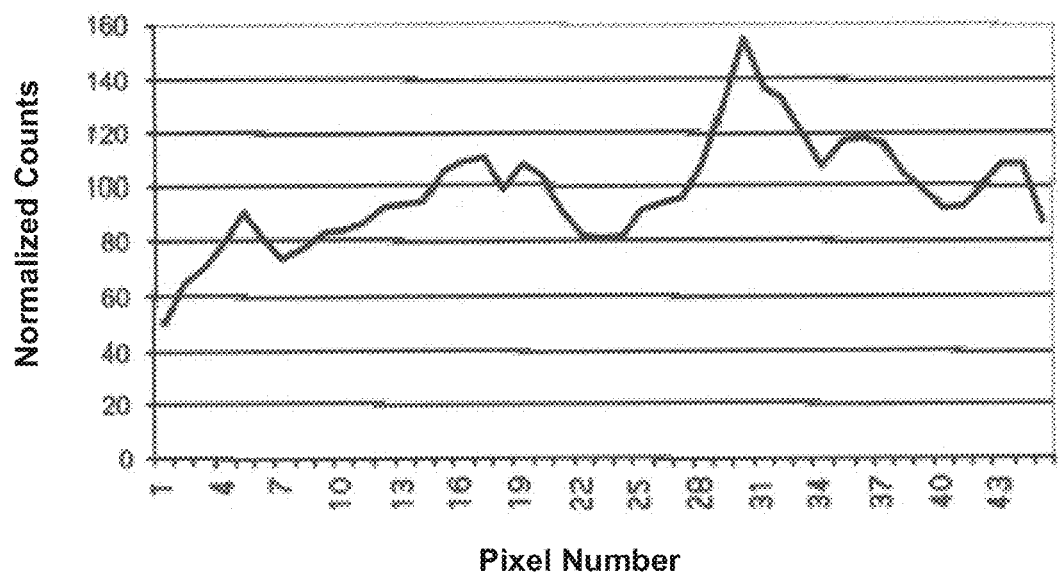

In the second portion of this experiment, the cylindrical phantom was loaded with the background solution and lesions used in the planar study. The SPECT images (plane thickness of about 0.5 cm) of the cylindrical phantom demonstrated visibility for the about 8 mm lesions, but failed to visualize the about 6 mm lesion although it was located only about 1 cm from the cylinder wall, as shown in FIG. 12A. In addition, the center mounting rod was seen in Panels III and IV as a vertical cold line through the center of the phantom. The lineout graphs in FIG. 12B are vertical profiles through the center of the about 8 mm lesions. In FIG. 12B, Panel I corresponds to Panel II in FIG. 12A and Panel II corresponds to Panel VII in FIG. 12A. Note that in Table 4, below, the SPECT S:N and contrast were comparable to that of the planar case (Table 3) for the about 8 mm lesions, but that the about 6 mm lesion is not seen in the SPECT images.

TABLE 4

|  | Frame 2 (8 mm) | Frame 7 (8 mm) | 6 mm lesion |
| --- | --- | --- | --- |
| Contrast | 0.48 | 0.55 | N/A |
| S:N | 4.80 | 5.50 | N/A |

As the lesion signal versus the lesion depth in "tissue" relationship became a more apparent limitation, a dual head detector concept was developed. The dual head system may be very useful in clinical situations where lesion location is not known a priori. This example demonstrated that two opposing about 5 minute to about 10 minute static views of the compressed breast combined by the geometric mean method produce a final image contrast comparable to that obtained from tomographic techniques. In addition, this method was significantly easier to clinically implement and required less imaging time than tomographic imaging. The opposed views may be obtained using a dual-head system or by repositioning a single detector head. In the latter case, an independent compression paddle system may enable stable breast imaging geometry while repositioning the detector head.

Specific Example 3

The patients enlisted in this study (N=55) were selected after a suspicious finding was reported in a routine X-ray screening mammogram. Using the mammographic films as guidance, the patients were placed on the stereotactic system table and the breast was compressed with a 5 cm×5 cm compression paddle (mean compression tissue thickness of about 5.96 cm, SD=about 1.41 cm). Scout views were obtained with the X-ray system until it was verified that the region-of-concern demonstrated in the mammogram was in the field-of-view. The mini gamma camera was then mounted to the X-ray system gantry in the needle driver position, see FIG. 1. A radiotracer was administered via venous puncture and an acquisition was initiated at the time of injection for about 10 minutes. Digital X-ray images were stored as high-resolution tiff images, and about 10-minute static gamma camera images were obtained for all patients. Additionally, dynamic data was stored in list mode for 33 of the 55 cases and radiotracer time uptake curves were generated for each of these cases. Each of the patients returned the following day for needle biopsy and these results are shown in Table 5, infra (the asterisked items indicate carcinoma).

TABLE 5

| Lesion Type | Number |
| --- | --- |
| *Ductal carcinoma-well differentiated | 6 |
| *Ductal carcinoma-moderately differentiated | 3 |
| *Mucinous carcinoma | 1 |
| *Ductal carcinoma in situ | 3 |
| Fibrocystic change | 22 |
| Fibrocystic change with microcalcifications | 12 |
| Fat necrosis | 1 |
| Sclerosing adenosis with microcalcifications | 2 |
| Atypical hyperplasia | 2 |
| Fibroadenoma | 3 |

In standard stereotactic needle biopsy procedures, X-ray densities such as dense masses, scar tissue and/or calcifications may be used to determine the optimal area for tissue biopsy; therefore, densities may indicate disease and their location may be spatially correlated to regions of diseased tissue.

Figure 13:
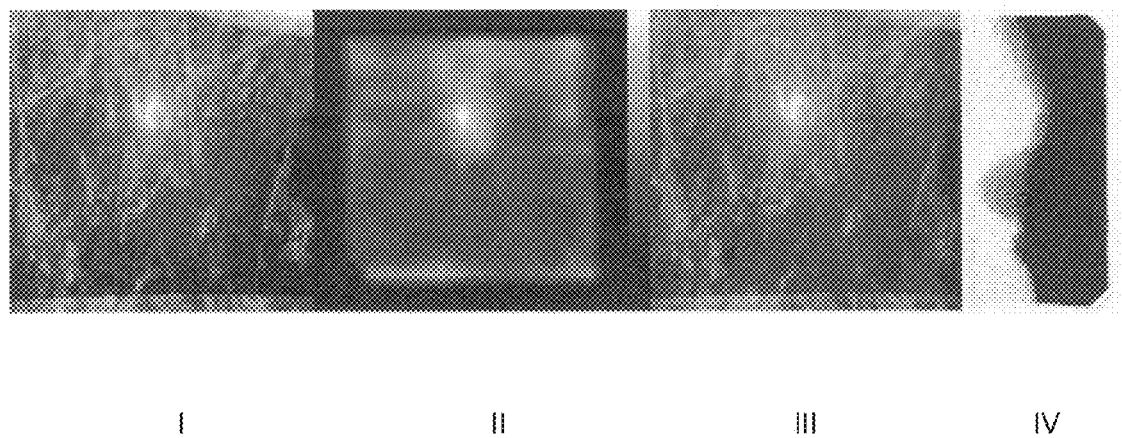
FIG. 13 shows an X-ray (Panel I), a gamma image (Panel II), and a coregistered and overlaid X-ray and gamma image (Panel III). Panel IV shows a standard camera image indicating a false negative study for this patient.
Figure 14:
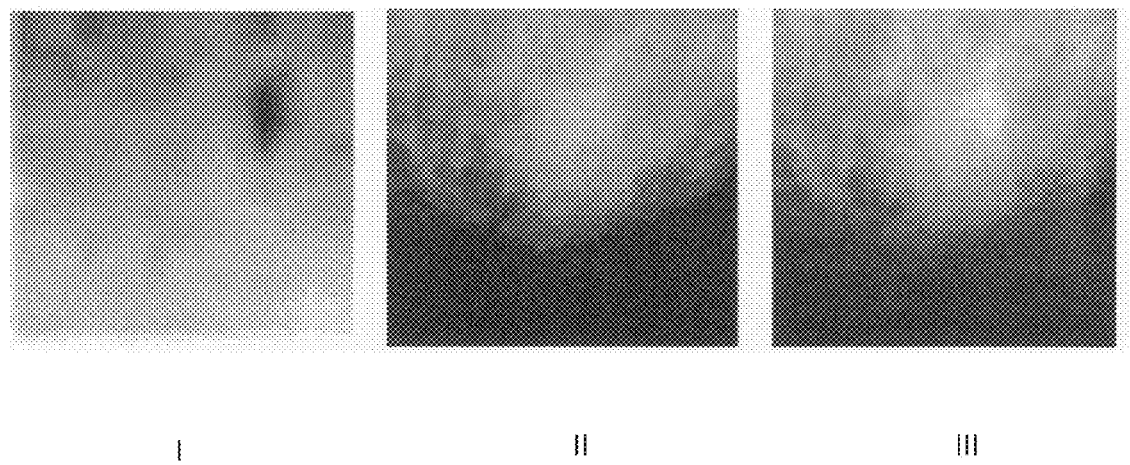
FIG. 14 shows radiotracer uptake in the gamma image (Panel I), suspicious microcalcifications in the X-ray image (Panel II), and an overly image demonstrating a poor spatial correlation of the images (Panel III).

A clinical study was conducted where each patient image set included a digital X-ray, a gamma image, and an overlay image for comparison (FIG. 13). Of the 55 studies completed, 25 demonstrated non-uniform radiotracer uptake allowing spatial comparison with the X-ray. Of these cases there were 13 cancers with focal uptake, 10 negative studies with low patchy uptake, and 1 false negative (mucinous carcinoma) with a photopenic region. Each image set was given a spatial registration agreement grade from I to III. Grade I representing high spatial correlation, Grade II good spatial correlation (less than about ±5 mm differential) and Grade III, poor correlation (greater than about ±5 mm differential). There were 18 Grade I, 5 Grade II and 2 Grade III cases. One of the Grade II studies was a ductal carcinoma case which presented as microcalcifications without defined mass in the X-ray image and focal radiotracer uptake in the gamma image. This focal uptake, however, was not superimposed with the calcifications (FIG. 14). In cases such as this, the scintimammography image may provide better localization for needle biopsy targeting. Both Grade III cases consisted of poorly correlated mild patchy uptake.

Figure 15:
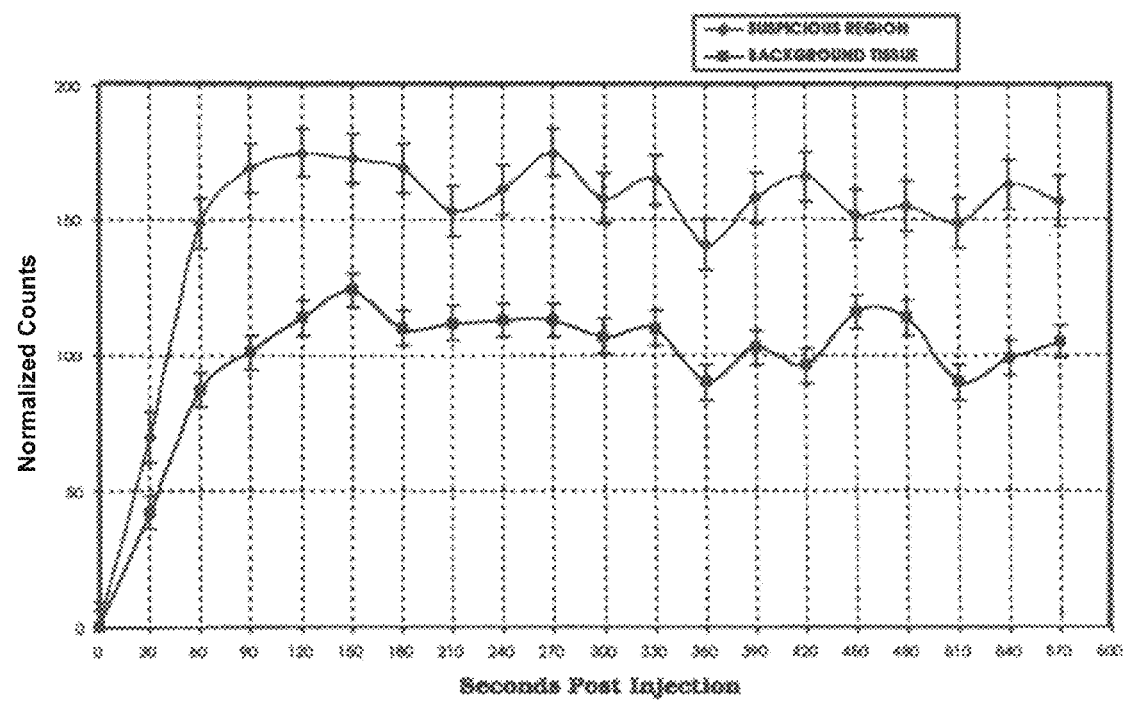
FIG. 15 shows an uptake curve where the lesion uptake is very high and this case was determined via needle biopsy to be an infiltrating ductal carcinoma with high nuclear grade.

Dynamic radiotracer uptake acquisitions are in wide use for several other nuclear medicine studies, but have not been investigated in this application due to the limitations of clinical instrumentation. The SFOV gamma camera designed for this system excluded extramammary radiotracer uptake from the acquisition and enabled a dynamic study of the tracer distribution in the breast tissue. List mode acquisitions for 33 patients were used to reconstruct time uptake curves with about a 30 second integration time per data point (FIG. 15). In FIG. 15, each graph contained a baseline tissue uptake curve (BKG) and an area-of-concern (AOC) uptake curve for about a 4 pixel (about 6.6 mm×about 6.6 mm) region. The AOC was drawn on the area of focal uptake for positive gamma images. For negative radiotracer studies, a region was spatially correlated with the location of radiodensity in the X-ray image. Of these 33 cases, 9 were infiltrating carcinoma, 2 were ductal carcinoma in situ, 1 was a fibroadenoma, and the remaining 21 were negative studies.

Evaluation of the dynamic data yielded several interesting observations. First, nearly all cases demonstrated an oscillation of counts in the range of about 30 second to about 60 second cycles for both the AOC and BKG regions. This oscillation was significantly greater than could be expected from statistical noise and may indicate some blood flow or transient redistribution effects. In addition, initial radiotracer uptake was rapidly occurring within the first 2 minutes, and it was determined that it is possible to obtain useful diagnostic images with this SFOV detector using about a 3 minute acquisition time. This acquisition time is significantly less than the about 10 minutes currently necessary for clinical scintimammographic and would allow greater compression to be used that in turn improves lesion contrast and therefore study sensitivity. Lastly and perhaps most significantly, the time uptake curves obtained in this study add to the diagnostic value of scintimammography by potentially distinguishing between false positive and true positive studies.

Figure 16:
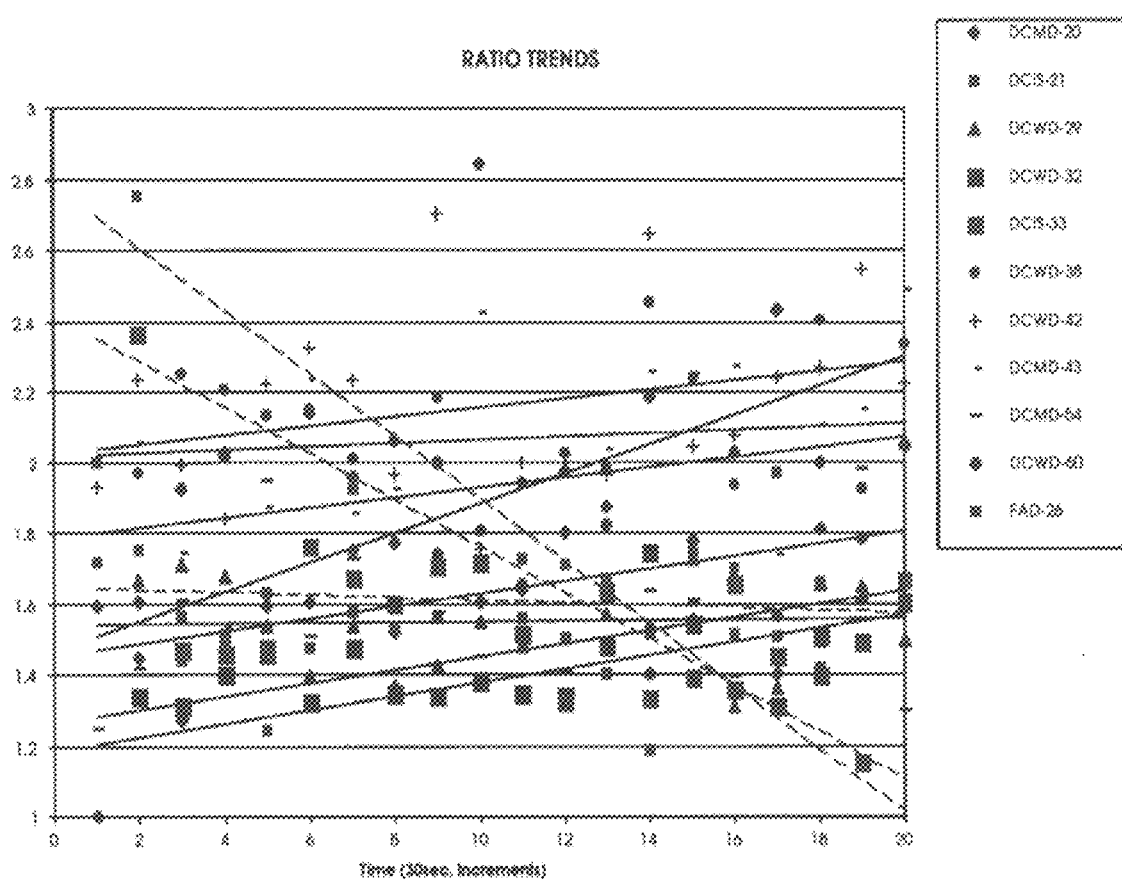
FIG. 16 is a graph showing data points for several of the true positive cases and for all of the false positive cases.

Several methods of evaluating the dynamic study data were tested. First, the rise time of the AOC to determine if there was a relationship between the slope of the uptake curve and lesion histology was evaluated, subsequently no correlation was found. In addition, contrast and signal-to-noise ratios were plotted as a function of time; no relationship between these values and tumor type was observed. Since both contrast and signal-to-noise ratios are based on subtracting the lesion signal from the background signal, it was hypothesized that calculations may not be sensitive enough to indicate minute trends in tracer uptake and washout. By plotting the ratio of the lesion ROI over the background ROI as a function of time and applying a linear fit to the data points of each case, it was observed that all true positives had an increasing linear trend and that all false positives had a negative linear trend (FIG. 16).

The data processing and analysis methods developed for this study positively impact the clinical value of scintimammographic studies. The results provided in this example may indicate that lesion malignancy can be determined with a high degree of accuracy without biopsy, see Table 2, infra.

TABLE 6

| | |
|---|---|
| True positive | 10 |
| True negative | 42 |
| False positive | 1 (1-epithelial hyperplasia) no uptake curve available |
| False negative | 1 (mucinous Ca) very low grade lesion |
| Sensitivity | 90.9% |
| Specificity | 97.7% |
| PPV | 90.9% |
| NPV | 97.7% |
| Accuracy | 94.5% |

Table 6 shows the results of 55 cases (only 33 of which contain uptake curves) showing the high negative predictive value. In sum, the less invasive nature of these studies spares the patient of physical and emotional trauma and would significantly reduce the cost of managing cases of suspicious mammographic studies.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the cellular and molecular biology fields or related fields are intended to be within the scope of the appended claims.

The disclosures of all references and publications cited above are expressly incorporated by reference in their entireties to the same extent as if each were incorporated by reference individually.

What is claimed is:

1. A method for controlling a device for determining a lesion location within a target site in a patient, the steps comprising:
   receiving a pair of images and associated pair of signal intensities, wherein the pair of images and pair of signal intensities are obtained simultaneously from multiple angles relative to the target site from a plurality of photon imaging devices; and
   determining a lesion location in the patient based upon the pair of images acquired by the plurality of photon imaging devices and the pair of signal intensities.

2. The method of claim 1, further comprising providing at least one gantry, wherein the plurality of photon imaging devices includes a first photon imaging device comprising an x-ray generator mounted on the at least one gantry and a second photon imaging device comprising an x-ray detector mounted on the at least one gantry, and further comprising providing a third photon imaging device comprising a gamma camera mounted on the at least one gantry.

3. The method of claim 2, further comprising providing a fourth imaging device comprising a gamma camera mounted on the at least one gantry.

4. The method of claim 3, wherein the at least one gantry is a plurality of gantries and the first photon imaging device and the third photon imaging device are each mounted on separate gantries, wherein the separate gantries are movable with respect to each another.

5. The method of claim 1, further comprising providing at least one gantry for mounting the plurality of photon imaging devices.

6. The method of claim 5, wherein the at least one gantry is a plurality of gantries and a first photon imaging device is a gamma camera mounted on a first gantry of the plurality of gantries, a second imaging device is an x-ray generator mounted on a second gantry of the plurality of gantries, and a third imaging device is an x-ray detector mounted on the second gantry.

7. The method of claim 6, further comprising providing a fourth photon imaging device comprising a gamma camera mounted on the first gantry.

8. The method of claim 6, wherein the first gantry and the second gantry comprise concentric rings moveable with respect to each other.

9. The method of claim 1, further comprising controlling movement of the plurality of photon imaging devices with respect to the target site such that the plurality of photon imaging devices obtains the pair of images at opposing positions.

10. The method of claim 9, wherein in the step of controlling movement of the plurality of photon imaging devices, the target site includes one or more sites selected from the group consisting of: breast, thyroid, parathyroid, heart, liver, kidney, gall bladder, bladder, reproductive organs and glandular structures.

11. The method of claim 1, wherein at least one of the signal intensities includes a comparative signal intensity calculated from at least one of: comparing changes in attenuation, comparing changes in spatial resolution and comparing changes in partial volume effect.

12. The method of claim 1, wherein at least one of the signal intensities includes a comparative signal intensity calculated from at least two of: comparing changes in attenuation, comparing changes in spatial resolution and comparing changes in partial volume effect.

13. The method of claim 1, wherein the step of determining determines the lesion location in the patient based upon the plurality of images acquired by the plurality of photon imaging devices and using only a single pair of signal intensities obtained simultaneously from opposing positions.

14. An apparatus for determining a lesion location within a target site in a patient, the apparatus comprising:
   at least one gantry;
   a plurality of photon imaging devices that receives a pair of images and associated pair of signal intensities, wherein the pair of images and pair of signal intensities are obtainable simultaneously from multiple angles relative to the target site;
   a controller configured to:
      control movement of the plurality of photon imaging devices mounted to the at least one gantry;
      receive the pair of images and the pair of signal intensities from the plurality of photon imaging devices; and
      determine a lesion location in the patient based upon the pair of images acquired simultaneously by the plurality of photon imaging devices and the pair of signal intensities.

15. The apparatus of claim 14, wherein the plurality of photon imaging devices includes an x-ray generator and an x-ray detector.

16. The apparatus of claim 14, wherein the plurality of photon imaging devices includes a gamma camera.

17. The apparatus of claim 14, wherein the controller is configured to calculate the lesion location within the target site based upon the pair of images and based upon a comparative signal intensity for the lesion calculated by using the pair of signal intensities received simultaneously from different angles relative to the target site.

18. The apparatus of claim 14, wherein the comparative signal intensity is calculated from at least one of: comparing changes in attenuation, comparing changes in spatial resolution and comparing changes in partial volume effect.

* * * * *